US009198872B2

(12) United States Patent
Stabler et al.

(10) Patent No.: US 9,198,872 B2
(45) Date of Patent: Dec. 1, 2015

(54) DENDRITIC AND HYPERBRANCHED POLYMERS FOR CELLULAR ENCAPSULATION AND FUNCTIONALIZATION

(75) Inventors: Cherie Stabler, Coral Gables, FL (US); Kerim Gattas-Asfura, Miramar, FL (US)

(73) Assignee: University of Miami, Miami, FL (US)

(*) Notice: Subject to any disclaimer, the term of this patent is extended or adjusted under 35 U.S.C. 154(b) by 214 days.

(21) Appl. No.: 13/532,340

(22) Filed: Jun. 25, 2012

(65) Prior Publication Data
US 2012/0328673 A1    Dec. 27, 2012

Related U.S. Application Data

(63) Continuation-in-part of application No. 12/633,270, filed on Dec. 8, 2009, now Pat. No. 8,728,520.

(60) Provisional application No. 61/120,711, filed on Dec. 8, 2008.

(51) Int. Cl.
A61K 9/50     (2006.01)
A61K 35/12    (2006.01)

(52) U.S. Cl.
CPC ............ *A61K 9/5031* (2013.01); *A61K 35/12* (2013.01)

(58) Field of Classification Search
USPC ........................................................ 424/400
See application file for complete search history.

(56) References Cited

U.S. PATENT DOCUMENTS

| | | |
|---|---|---|
| 4,353,888 A | 10/1982 | Sefton |
| 4,673,566 A | 6/1987 | Goosen et al. |
| 4,689,293 A | 8/1987 | Goosen et al. |
| 4,806,355 A | 2/1989 | Goosen et al. |
| 4,923,645 A | 5/1990 | Tsang et al. |
| 5,334,640 A | 8/1994 | Desai et al. |
| 5,410,016 A | 4/1995 | Hubbell et al. |
| 5,550,178 A | 8/1996 | Desai et al. |
| 5,700,848 A | 12/1997 | Soon-Shiong et al. |
| 5,705,270 A | 1/1998 | Soon-Shiong et al. |
| 5,762,959 A | 6/1998 | Soon-Shiong et al. |
| 5,766,907 A | 6/1998 | Chang et al. |
| 5,777,062 A | 7/1998 | Pugin |
| 6,255,448 B1 | 7/2001 | Grimaldi et al. |
| 6,258,870 B1 | 7/2001 | Hubbell et al. |
| 6,911,227 B2 | 6/2005 | Hubbell et al. |
| 7,534,649 B2* | 5/2009 | Lehman et al. ............... 438/106 |
| 8,097,343 B2* | 1/2012 | Mahmud et al. ............. 428/446 |
| 8,728,520 B2 | 5/2014 | Stabler et al. |
| 2007/0196454 A1 | 8/2007 | Stockman et al. |
| 2007/0260037 A1 | 11/2007 | Hsu |
| 2009/0170179 A1* | 7/2009 | Lynn et al. ................... 435/180 |

OTHER PUBLICATIONS

Jones, et al., Al H., S. (2003) "Nano-encapsulation of furosemide microcrystals for controlled drup release." J Control Release 89: 59-68.

Chong, et al. (2009). "A paradigm for peptide vaccine delivery using viral epitopes encapsulated in degradable polymer hydrogel capsule." Biomaterials 30 (28): 5179-5186.
Johnston. et at., (2006). "Layer-by-Layer engineered capsules and their applications." Current Opinion in Colloid & Interface Science 11(4): 203-209.
Kumar, et al. (2009). Encapsulation & release of capsules. Materials Science & Engineering release of rifampicin using polyvinyl pyrrolidone}-poly(rmethacylic C 29(8)2508-2513 microcapsules built by layer by layer assembly for the B: Biointenaces 65(2):55 53 on the drag release properties of polysaccharide multtayers is.
Manju, S. and K. Screenivasan (2011). "Hollow microcapsules built by layer by layer assembly for the encapsulation and sustained release of curcumin." Colloids and Surfaces B: Biointerraces 85(2): 588-593.
Qui, D., S. Leporatl, et al. (2001). "Studies on the drug release properties of polysaccharide multilayers encapsulated Ibuprofen microparticles," Lagmuir 17: 5375-5380.
Zhao, Q., B. Han, et al., (2007). "Hollow chitosan-alginate multilayer microcapsules as drug delivery vehicle: doxorubiein loading and in vitro and in vivo studies." Nanomedicine: Nanotechnology, Biology and Medicine 3(1): 63-74.
Gatas-Ahfura, et al., (2003). "Bioorthogonal layer-by-Layer Encapsulation of Pancreatic Islats via Hyperbranched Polymers." 2013 American Chemical Society., 5, p. 1954-9974.
Paez, et al. (2012). "Dendritic polyglycarolamine as a functional antifouling coating of gold surfaces". 19188/J. Mater. Chem., 2012, 22, 19488-19497.
Zhou, et al. (2010). "Self-Assembly of Hyperbranched Polymers and Its Biomedical Applications." Advanced Materials. 2010, 22, 4567-4590.
Gao, et al. (2003). "Hyperbranched polyer: from synthesis to applications." Science Direct. 2004. Prog. Polym. Sci. 29 (2004) 183-275.
Opsteen, et al. Modular synthesis of block copolymers via cycloaddition of terminal.
Crescenzi, et al. (2001) "Novel Bydrogels via Click Chemisty: Synthesis and Potential Biomedical Applications," American Chemical Society: A-G.
Eiselt, et al. (1999) "Rigidity of Two-component Hydrogels Prepared from Algenate and Poly (ethylane glycol)-Diamines", Macromolecules. 32: 5561-5566.

(Continued)

*Primary Examiner* — Gina Justice
(74) *Attorney, Agent, or Firm* — Malloy & Malloy, P.L.

(57) ABSTRACT

A protective coating for covering a biological material, the protective coating having a plurality of interconnected layers covalently bonded to each other. The plurality of interconnected layers can include at least one hyperbranched polymeric material, and at least one dendrimer. A method of forming a protective coating for covering a biological material, the method can include depositing a plurality of interconnected layers, which are covalently bonded to each other. The plurality of interconnected layers can include at least one hyperbranched polymeric material, and at least one dendrimer.

7 Claims, 14 Drawing Sheets

(56) References Cited

OTHER PUBLICATIONS

Huang, et al. (2009) "Using Click Chtmistry to Fabricate Ultrathin Thermoresponsive Microcapsules through Direct Covalent Layer-by-layer Assembly", Macromolecules. 82: 5155-5166.

Stabler, et al. (2007) "Surface Re-engineering of Pancreatic Islets with Recombinant azido-Thrombomodulin", Bioconjugate Chemistry. 18: 1713-1715.

Wilson, et al. (2008) "Layer-by-Layer Assembly of conformal Nanthin PEG Coating for Intraportal Islet Transplantation", Nano Letters. 8 (8): 1940-1948.

\* cited by examiner

Functionalized PAMAM G2

Hyperbranched Azido-Functionalized Alginate

DENDRITIC AND HYPERBRANCHED POLYMERS FOR CELLULAR ENCAPSULATION AND FUNCTIONALIZATION

CROSS-REFERENCE TO RELATED APPLICATIONS

This application is a Continuation-In-Part of U.S. patent application Ser. No. 12/633,270, titled "Cross-linked Alginate-Polyalkylene Glycol Polymer Coatings for Encapsulation and Methods of Making the Same" filed on Dec. 8, 2009, which claims priority from U.S. Provisional Patent Application No. 61/120,711, titled "Crosslinked Alginate-PEG Polymers for Cellular Encapsulation" and filed on Dec. 8, 2008. Both U.S. patent application Ser. No. 12/633,270 and U.S. Provisional Patent Application No. 61/120,711 are hereby incorporated by reference in its entirety.

FIELD OF THE INVENTION

The present invention is generally directed toward crosslinked alginate-polyalkylene glycol polymer coatings for encapsulation of particles and cells and methods of making the same. More specifically, the present invention relates to polymeric functional materials for conformal coating and functionalization of biological surfaces.

BACKGROUND OF THE INVENTION

Cellular encapsulation has been a subject of research for several decades as a means to mask transplanted cells from the in vivo host. By coating the cells with a highly biocompatible layer, surface antigens, inflammatory proteins, and other agents that may instigate an immune/inflammatory response may be dampened or eliminated. In order to develop a reasonable method to encapsulate a cell, the process must not be detrimental to the cells and result in a highly biostable and biocompatible coating. Cellular encapsulation through the use of highly purified alginate has shown significant promise. In fact, clinical trials using islets within alginate capsules in the absence of an immunosuppression regimen are ongoing worldwide. However, to date, studies using this approach have failed because 1) the resulting gels are unstable; and 2) the resulting coating prevents adequate nutrient delivery for highly metabolically active cells, such as islets of Langerhans.

Various permutations of alginate and/or PEG encapsulation of mammalian cells has been patented, including U.S. Pat. Nos. 4,353,888; 4,673,566; 4,689,293; 4,806,355; 4,923,645; 5,762,959 and 5,766,907). However, most of these methods produce alginate gels that degrade over time due to leakage of divalent cations.

Additional research has been conducted to attempt to increase the stability of alginate and/or PEG-based gels through the use of covalent cross-linking. For example, free radical polymerization generation of capsules to entrap mammalian cells has been disclosed in U.S. Pat. Nos. 5,334,640; 5,410,016; 5,700,848; 5,705,270; and 6,258,870. However, these techniques have not proven useful because these methods induce moderate to severe cell damage, particularly for cells that are vulnerable to oxidative stress, such as islets of Langerhans.

Layer-by-layer coating of thin films has multiple biomedical applications, from enhancing biocompatibility of an inert implant, to immune-camouflage of a cellular transplant, to local drug delivery.

Layer-by-layer encapsulation has been used for temporal drug delivery for multiple applications. Drug microcrystals, proteins, or enzymes can be encapsulated and the rate of release can be modified through the properties of the coating and their subsequent thickness. Furthermore, the overall polymer load is substantially reduced, given that the thickness of the coating can be intricately controlled. Agents may be encapsulated in their crystalline form, or via infiltration into a matrix that is subsequently coated. Of note, recent published applications of layer-by-layer methods for drug delivery include: ibuprofen, furosemide, doxorubicin, rifampicin, curcumin, or even peptides or enzymes.

SUMMARY OF THE INVENTION

Polymers according to various embodiments have flexibility in their hydrophobicity (through the phosphine/MCT group), their charge (positive or neutral), and their overall thickness through layer assembly. This provides a versatile platform for application to numerous drugs, such as those mentioned in the examples given above. Furthermore, the ease in which the surface of these coatings may be functionalized with various antibodies or antigens permits for the targeting and, if desired, phagocytosis, of these drug eluting materials to specific cells.

In one embodiment, the invention is drawn to a biocompatible capsule having a biological material and a covalently stabilized coating encapsulating the biological material. The covalently stabilized coating can be formed by reacting (i) alginate—[polyalkylene glycol (PAG)-$X^1$]$_n$, and (ii) multifunctional PAG-$X^2$, to form covalent bonds, wherein n is an integer greater than 0, a first one of $X^1$ and $X^2$ is $N_3$, and a second one of $X^1$ and $X^2$ is selected from the group consisting of:

(a)

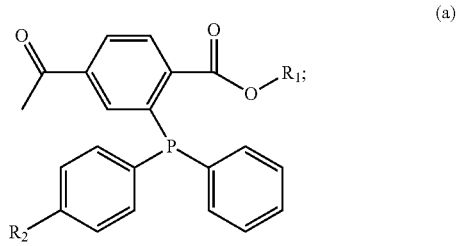

(b) —C≡C; and (c)

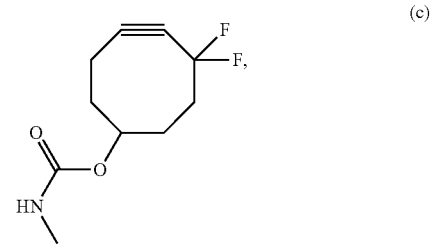

wherein $R^1$=$CH_3$, $CH_2CH_3$, $CH(CH_3)_2$, or

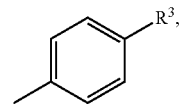

$R^2$=N(CH$_3$)$_2$, OCH$_3$, OH, CH$_3$, H, F, Cl, Br or NO$_2$, and $R^3$=OCH$_3$, CH$_3$, H, F, C$_1$ or NO$_2$.

The biological material can include a material selected from the group consisting of cells, pharmaceuticals, biological agents, biopolymers, RNA, DNA and fragments of DNA or RNA. The cells can be islets of Langerhans.

The covalently stabilized coating can include a plurality of monolayers. The covalently stabilized coating can be covalently bonded to the biological material. The plurality of monolayers alternate between monolayers of Alginate—[PAG-X$^1$]$_n$ reaction products and monolayers of multi-functional PAG-X$^2$ reaction products. The multi-functional PAG-X$^2$ comprises a multi-arm PAG-X$^2$ having at least three PAG-X$^2$ arms.

The alginate—[polyethylene glycol (PAG)-X$^1$], molecule, the multi-functional PAG-X$^2$ molecule, or both, can also include an additional terminal ligand, X$^3$. The additional terminal ligand, X$^3$, can be selected from the group consisting of proteins, imaging labels, nanoparticles, biopolymers, RNA, DNA, and fragments of RNA or DNA.

The coating can be covalently bonded to the biological material by reacting a first terminal ligand of compound (A) with amino groups on a surface of the biological material. Compound (A) can include:
the first terminal ligand comprising

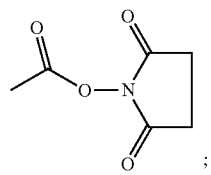

and
a second terminal ligand comprising a ligand selected from the group consisting of:

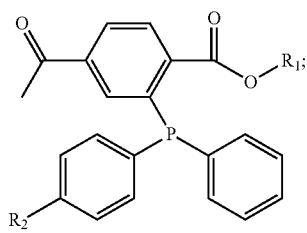 (a)

(b) —C≡C;
(c) —N$_3$; and

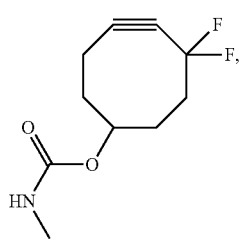 (d)

In compound (A), R$^1$ can be CH$_3$, CH$_2$CH$_3$, CH(CH$_3$)$_2$, or

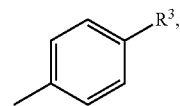

R$^2$ can be N(CH$_3$)$_2$, OCH$_3$, OH, CH$_3$, H, F, Cl, Br or NO$_2$, and R$^3$ can be OCH$_3$, CH$_3$, H, F, C$_1$ or NO$_2$.

The invention is also drawn to a method of forming the biocompatible capsule described above by reacting (i) alginate—[polyalkylene glycol (PAG)-X$^1$]$_n$, (ii) multi-functional PAG-X$^2$, or (iii) both, in an aqueous solution containing the biological material. The reacting step can proceed without a free-radical initiator. The reacting step can produce a covalent bond resulting from reacting an X$^1$ ligand of said alginate—[PAG-X$^1$]$_n$ with an X$^2$ ligand of said multi-functional PAG-X$^2$. The reacting step can include adding molecular monolayers of either alginate—[PAG-X$^1$]$_n$ or multi-functional PAG-X$^2$.

According to various other embodiments, the coatings can have a highly branched architectural design. Such coatings can be used to build protective coatings on cells, cell clusters, or other bioactive agents, in this way allowing enhanced control over the physical, chemical, and biological properties of the coating. In addition, the unique branched system provides for a high degree of surface presentation of agents, thereby providing a novel platform for the chemoselective presentation of a large amount of agents on the surface of the coating (which could be highly beneficial for targeting, labeling, or as a bioactive interface).

One embodiment relates to a protective coating for covering a biological material, the protective coating having a plurality of interconnected layers covalently bonded to each other. The plurality of interconnected layers can include at least one hyperbranched polymeric material, and at least one dendrimer. The protective coating can also include at least one biologically-active agent chemoselectively presented on a surface of the coating. The biologically-active agent can be selected from a targeting agent, a labeling agent, a bioactive interface, and combinations thereof. The protective coating can have a thickness of less than 10 nm. The biological material can be selected from a plurality of cells, a plurality of cell clusters, a plurality of bioactive agents, and combinations thereof.

Another embodiment relates to a method of forming a protective coating for covering a biological material, the method can include depositing a plurality of interconnected layers, which are covalently bonded to each other. The plurality of interconnected layers can include at least one hyperbranched polymeric material, and at least one dendrimer. The method can also include applying at least one biologically-active agent onto a surface of the coating. The biologically-active agent can be selected from a targeting agent, a labeling agent, a bioactive interface, and combinations thereof. The protective coating can have a thickness from 1 nm to up to 1000 nm. The biological material can be selected from a single cell, a plurality of cells, a plurality of cell clusters, a plurality of bioactive agents, and combinations thereof.

The coating systems according to various embodiments can be particularly applicable to the coating of drugs for stabilization or targeting—given the benign nature of the coating and the resulting coating stability.

These and other embodiments are described in more detail below.

BRIEF DESCRIPTION OF THE DRAWINGS

A fuller understanding of the present invention and the features and benefits thereof will be obtained upon review of the following detailed description together with the accompanying drawings, in which:

FIGS. 8(C) and (D) are height and deflection images, respectively, of Corning amino glass functionalized with a layer of Azide-PEG-NHS [5] followed by a layer of 4DiP-PEG [3].

DETAILED DESCRIPTION

Figure 1:
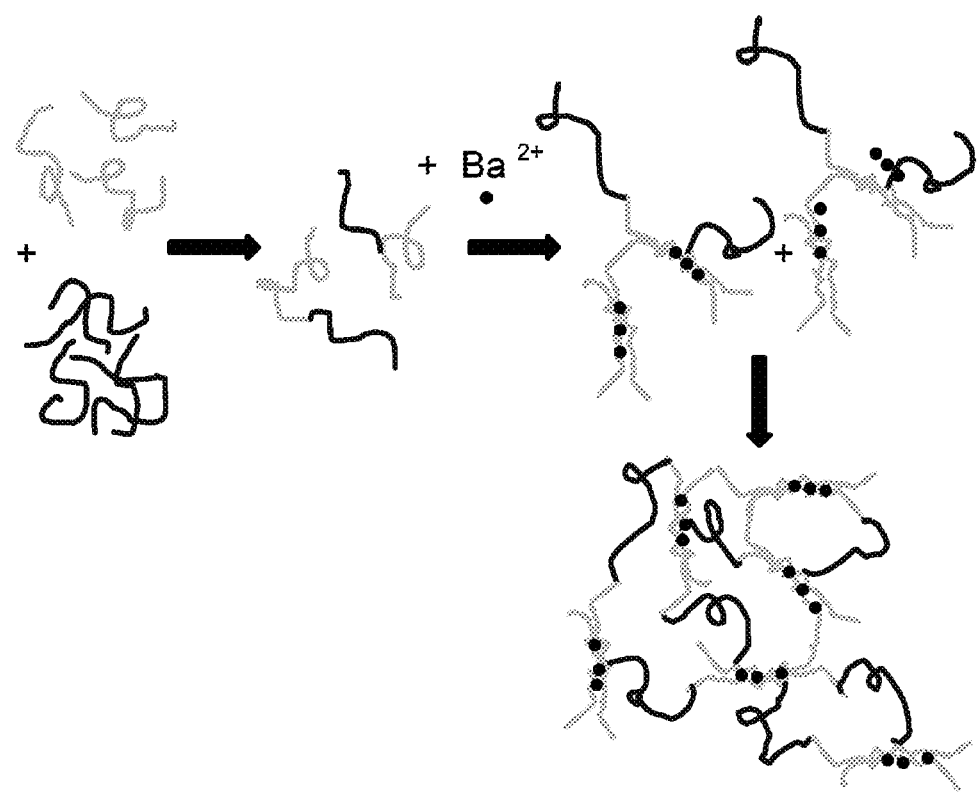
FIG. 1 is a schematic showing a gel and lock mechanism useful for producing encapsulated particles of the invention.

The invention is drawn to customized cross-linked alginate-polyalkylene glycol (PAG) polymer coatings for encapsulating biological materials and methods of applying the same. The polymer coatings are produced using a step-wise, chemoselective ligation scheme that does not require a free-radical initiator or elevated temperature. The techniques disclosed herein enable application of molecular monolayers of the alginate-PAG coatings on the biological materials. These monolayer coatings can be on the order of nanometers in thickness. It has been unexpectedly discovered that the coatings disclosed herein enable application of a coating that prevents rejection of coated cells by a host organism, such as a human, without causing premature death of encapsulated cells.

In one embodiment, the invention is drawn to a biocompatible capsule that includes a biological material and a covalently stabilized coating encapsulating the biological material. The covalently stabilized coating can be formed by reacting:

alginate—[polyalkylene glycol-$X^1$]$_n$, and multi-functional polyalkylene glycol-$X^2$, to form covalent bonds.

In the above formulas, the molecular weight of the polyalkylene glycol (PAG) can be between 500 and 250,000 Daltons; the polyalkylene glycol can be polyethylene glycol (PEG), polypropylene glycol (PPG) or a copolymer (PEG-PPG) thereof; n can be an integer greater than 0; a first one of $X^1$ and $X^2$ can be $N_3$; and a second one of $X^1$ and $X^2$ can be selected from the group consisting of:

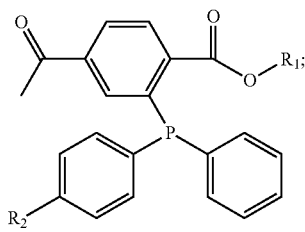

—C≡C; and

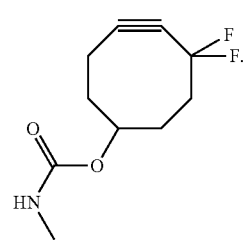

In ligands (a), (b) and (c) above, $R^1$=$CH_3$, $CH_2CH_3$, $CH(CH_3)_2$, or

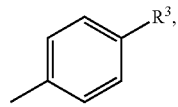

$R^2$=$N(CH_3)_2$, $OCH_3$, OH, $CH_3$, H, F, Cl, Br or $NO_2$, and $R^3$=$OCH_3$, $CH_3$, H, F, $C_1$ or $NO_2$.

In some embodiments, ligands (a), (b) and (c) above, $R^1$=$CH_3$, $CH_2CH_3$ or $CH(CH_3)_2$, and $R^2$=$N(CH_3)_2$, $OCH_3$, OH, $CH_3$ or H. In other embodiments, for ligands (a), (b) and (c) above, $R^1$=$CH_3$, and $R^2$=$N(CH_3)_2$, $OCH_3$, OH, $CH_3$ or H.

In some embodiments, n can be greater than 1, or n can be greater than 3, or n can be greater than 10, or n can be greater than 20. In some embodiments, the molecular weight of the polyalkylene glycol can be 750 to 100,000 Daltons, or 750 to 50,000 Daltons, or 1,000 to 25,000 Daltons, or 1,000 to 15,000 Daltons. Exemplary polyalkylene glycols include, but are not limited to polyethylene glycol, polypropylene glycol, polybutylene glycol and copolymers thereof.

As used herein, "encapsulating" is used to refer to a coating that completely surrounds and physically separates the encapsulated material from the surrounding environment. An encapsulating coating can be continuous and can have sufficient permeability to enable an encapsulated cell to transfer nutrients, waste, and oxygen with the surround environment while preventing an adverse immune response by an animal in which the encapsulated cell is implanted.

As used herein, "multi-functional" is used to refer to a molecule having more than one terminal ligand capable of forming a covalent bond or serving as an additional agent, for example an engineered protein, a fluorescent marker, a nuclear label, or a nanoparticle. In particular, the multi-functional molecules disclosed herein generally include at least one terminal ligand capable of forming a covalent bond via Staudinger ligation chemistry, copper-catalyzed Click chemistry or copper-free Click chemistry.

Although described as (i) alginate—[polyalkylene glycol-$X^1$]$_n$ and (ii) multi-functional polyalkylene glycol-$X^2$, it should be noted that the linkages between these molecular constituents can be direct or can be via a linking group. For example, the polyalkylene glycol in formulas (I) or (ii) can be connected to the terminal ligand, $X^1$ and $X^2$, respectively, via a linking group. Exemplary linking groups include, but are not limited to, alkanes, alkenes, alkynes, ethers, esters, amines, thiols, or combinations thereof.

The alginate—[PAG)-$X^1$]$_n$ molecule or the multi-functional PAG-$X^2$ molecule can also include an additional terminal ligand, $X^3$. The terminal ligand, $X^3$, can be selected from the group including, but not limited to, proteins, imaging labels, nanoparticles, biopolymers, RNA and DNA.

By definition, the multi-functional PAG-$X^2$ compound has at least two PAG-$X^2$ arms. The multi-functional PAG-$X^2$ can be a multi-arm PAG-$X^2$ having at least three PAG-$X^2$ arms, at least four PAG-$X^2$ arms or at least eight PAG-$X^2$ arms. In some embodiments, the multi-functional PAG-$X^2$ can have two or three PAG-$X^2$ arms and one or two arms with different functionalities, $X^3$, such as a fluorescein, a nanoparticle, or a PAG-fluorescein.

The biological material can be a cell, a cluster of cells, pharmaceuticals, biological agents, or a combination thereof. Generally, the biological materials will be cells or particles having a diameter less than 10 μm, or less than 1 μm, or less than 0.5 μm, or less than 50 nanometers.

The biological material can be a cell or a cluster of cells. Exemplary cells that can be used in the microcapsules and methods disclosed herein include, but are not limited to, islets of Langerhans, dopamine secreting cells, nerve growth factor secreting cells, hepatocytes, adrenaline/angiotensin secreting cells, parathyroid cells and norepinephrine or metencephalin secreting cells.

Figure 9:
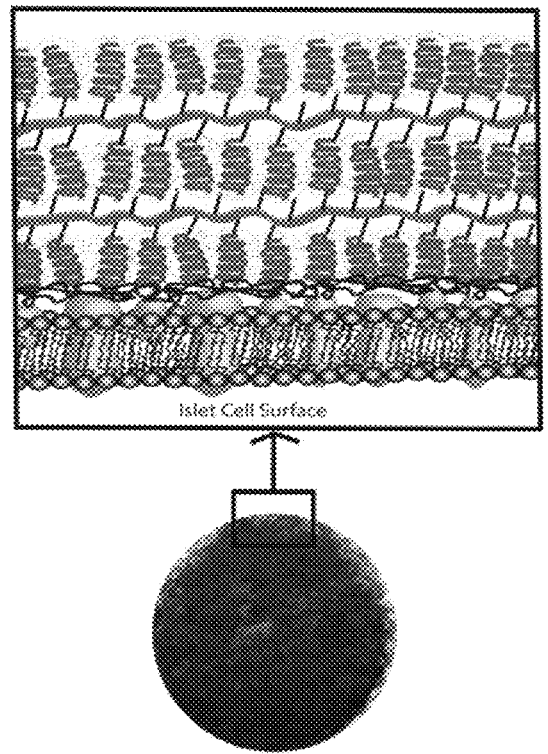
FIG. 9 shows a schematic representation of covalently linked layers of triarylphosphine PEG active ester (base layer), azido-alginate (interconnecting layer) and bi-triarylphosphine PEG (interconnecting layer and terminal layer).
Figure 10:
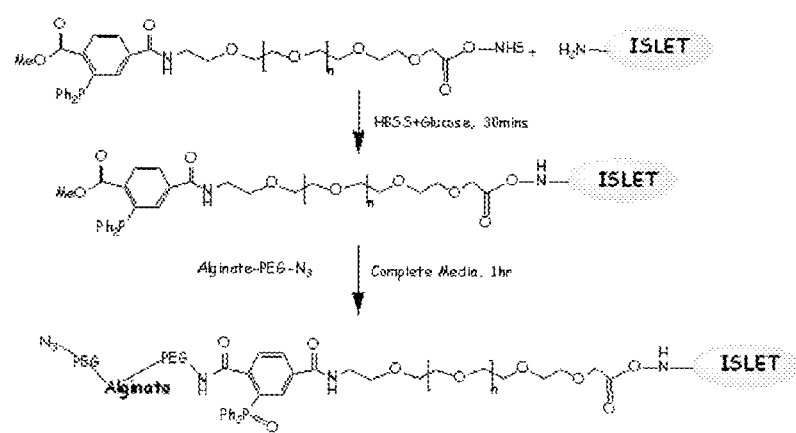
FIG. 10 shows a chemical scheme outlining the reactions for the covalent linking of two layers (triarylphosphine PEG active ester and azido-alginate) on the islet surface.

The covalently stabilized coating can include a plurality of monolayers of polymer material. As used herein, "monolayers" refer to molecular layers of polymer material (e.g., Alginate—[PAG-$X^1$]$_n$ reaction products and multi-functional PAG-$X^2$ reaction products) that are continuous. Monolayers are generally produced by step-growth techniques where one molecular layer of reactant is applied to a surface at a time, such as where one of two reactant species of a Staudinger ligation are dissolved in a solution and the other reactant species is bound to the surface being coated. Examples of molecular monolayers are shown in FIGS. 9 and 10.

Monolayers can be contrasted with layers formed by bulk polymerization, such as free-radical polymerization or where both reactants of a Staudinger ligation are dissolved in a single solution. In bulk polymerization, the reactions can happen in a random order and will not form molecular layers of polymer that are continuous. Rather, a layer produced by bulk polymerization will be thicker than a molecular monolayer and will include a mixture of the reactants without the order of a molecular monolayer.

In one embodiment, the plurality of monolayers can alternate between monolayers of Alginate—[PAG-$X^1$]$_n$ reaction products and monolayers of multi-functional PAG-$X^2$ reaction products. As used herein, "reaction products" refer to polymers resulting when $X^1$ and $X^2$ react to form a covalent bond. Examples are shown schematically in FIG. 10.

In another embodiment, a bulk layer and one or more monolayers can be applied to a biological material. For example, a monolayer can be applied to covalently bond the coating to the cell and then a bulk layer can be applied over the base monolayer.

The covalently stabilized coating can be at least one molecule thick, e.g., at least 0.1 nanometer thick. The covalently stabilized coating can be less than 300 microns thick, or less than 200 microns thick, or less than 100 microns thick, or less than 50 microns thick, or less than 25 microns thick, or less than 10 microns thick, or less than 1 micron thick.

The covalently stabilized coating can be covalently bonded to the biological material. The coating can be covalently bonded to the biological material by reacting a first terminal ligand of compound (A) with amino groups on a surface of the biological material. Compound (A) can include:

a first terminal ligand comprising

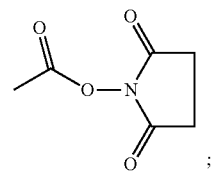

and
a second terminal ligand comprising a ligand selected from the group consisting of:

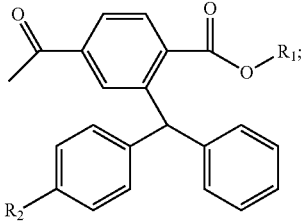

—C≡C;
—N$_3$; and

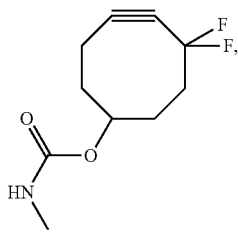

In compound (A), R$^1$ can be CH$_3$, CH$_2$CH$_3$, CH(CH$_3$)$_2$, or

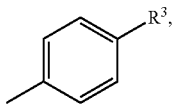

R$^2$ can be N(CH$_3$)$_2$, OCH$_3$, OH, CH$_3$, H, F, Cl, Br or NO$_2$, and R$^3$ can be OCH$_3$, CH$_3$, H, F, C$_1$ or NO$_2$.

Compound (A) can include a variety of ligands intermediate to the first and second terminal ligand. Exemplary intermediate ligands include PAGs, such as polyethylene glycol, polypropylene glycol and copolymers thereof.

In another embodiment, the invention is drawn to a method of forming the biocompatible capsules disclosed herein. The method can include forming a covalently stabilized coating encapsulating a biological material. The forming step can include providing an aqueous solution having the biological material suspended therein, where the aqueous solution also includes a reactant dissolved therein. The dissolved reactant can include (i) alginate—[PAG-X$^1$]$_n$, (ii) multi-functional PAG-X$^2$, or (iii) both. The method can also include reacting alginate—[PAG-X$^1$]$_n$ with multi-functional PAG-X$^2$ in the aqueous solution, wherein n is an integer greater than 0, a first one of X$^1$ and X$^2$ is N$_3$, and a second one of X$^1$ and X$^2$ is selected from the group consisting of:

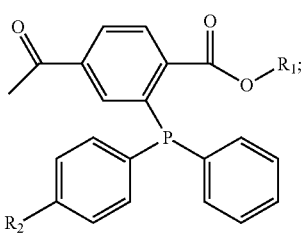

—C≡C; and

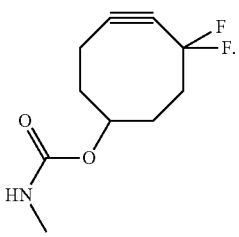

In the above formulas of (a), (b) and (c), R$^1$, R$^2$ and R$^3$ have the same meanings used throughout this disclosure. The reacting step can occur between approximately 40° C. and 20° C. For example, reacting step can occur at between about 33° C. and 40° C., or at room temperature, such as approximately 21 to 27° C.

The reacting step can produce a covalent bond resulting from reacting an X$^1$ ligand of the alginate—[PAG-X$^1$]$_n$ with an X$^2$ ligand of the multi-functional PAG-X$^2$. In one embodiment, the aqueous solution can include either alginate—[PAG-X$^1$]$_n$ or multi-functional PAG-X$^2$, but not both, and the covalently stabilized coating can include alginate—[PAG-X$^1$]$_n$, multi-functional PAG-X$^2$, or both. In such an instance, the reacting step can form a surface monolayer by:

reacting alginate—[polyalkalene glycol (PAG)-X$^1$]$_n$ dissolved in the aqueous solution with multi-functional PAG-X$^2$ in the covalently stabilized coating, thereby adding an alginate—[PAG-X$^1$]$_n$ surface monolayer to the covalently stabilized coating, or reacting multi-functional PAG-X$^2$ dissolved in the aqueous solution with alginate—[PAG-X$^1$]$_n$, in the covalently stabilized coating, thereby adding a multi-functional PAG-X$^2$ surface monolayer to the covalently stabilized coating.

The forming step can also include rinsing a product of the reacting step to remove unreacted reactant from the biological material and then isolating an intermediate biocompatible capsule. Following the rinsing step, the forming step can include, adding an additional surface monolayer to the intermediate biocompatible capsule. If the surface monolayer is an alginate—[PAG-X$^1$]$_n$ surface monolayer, the adding step can include reacting multi-functional PAG-X$^2$ dissolved in an aqueous solution with the alginate—[PAG-X$^1$]$_n$ in the surface monolayer. If the surface monolayer is a multi-functional PAG-X$^2$ surface monolayer, the adding step can include reacting alginate—[PAG-X$^1$]$_n$ dissolved in an aqueous solution with multi-functional PAG-X$^2$ in the surface monolayer. As used herein, "surface monolayer" refers to the molecular monolayer on the outside of the covalently stabilized coating or the intermediate biocompatible capsule.

The forming step can also include covalently bonding a base layer of the covalently stabilized coating to a surface of the biological material. In such an instance, the forming step can include providing an aqueous solution having the biological material suspended therein, where the aqueous solution includes compound (A) dissolved therein. Compound (A) can then be reacted with amino groups on the surface of the biological material. Compound (A) can include:
a first terminal ligand comprising

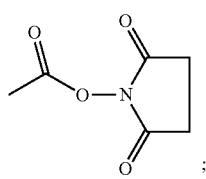

and
a second terminal ligand comprising a ligand selected from the group consisting of:

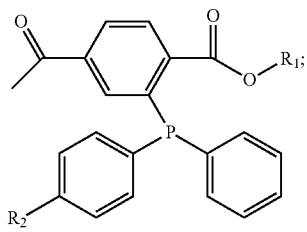

—C≡C;
—N$_3$; and

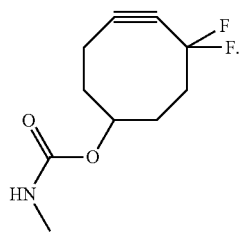

In the above formulas of (a), (b), (c) and (d), R$^1$, R$^2$ and R$^3$ have the same meanings used throughout this disclosure.

The forming step, the reacting step, or both can proceed without a free-radical initiator. It has been determined that the step-wise application of polymer layers disclosed herein has at least two benefits. First, many free-radical initiators, such as those relying on electromagnetic radiation, can produce moderate to severe cell damage. Second, it is possible to create the encapsulating coating using molecular monolayers of alginate and PAG.

Figure 2:
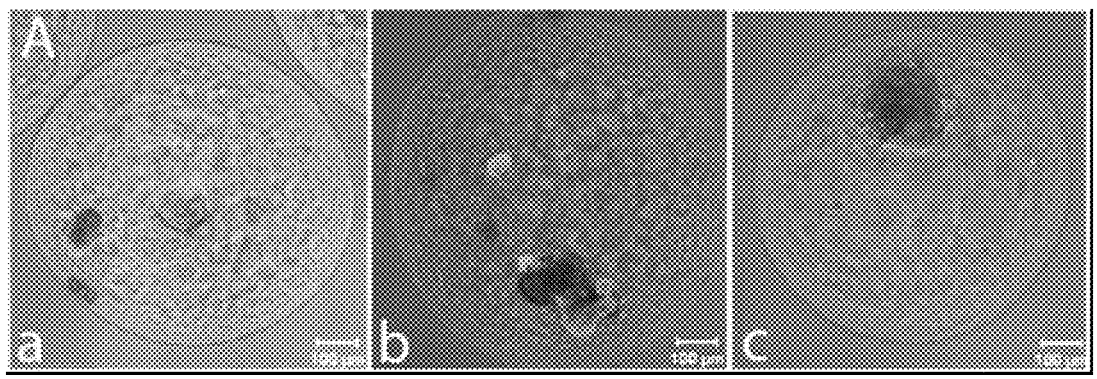
FIGS. 2(A)-(C) show confocal images of encapsulated Lewis rat islets stained using a Live/Dead fluorescent kit where live cells are labeled green and dead cells are labeled red.
Figure 3:
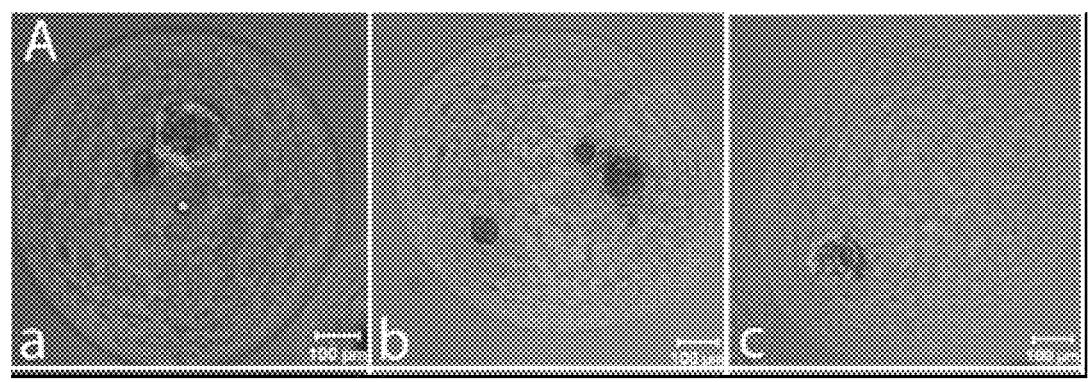
FIG. 3(A)-(C) show confocal images of encapsulated human islets stained using a Live/Dead fluorescent kit where live cells are labeled green and dead cells are labeled red.
Figure 4:
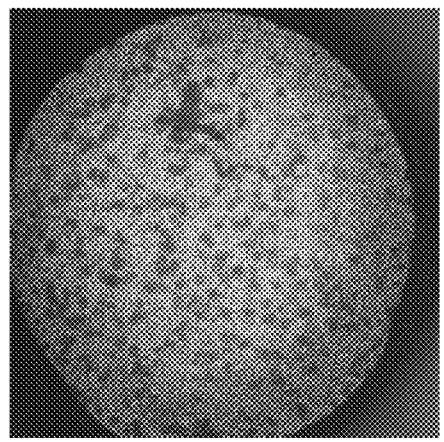
FIG. 4 shows confocal image of alginate-azide microcapsules with covalent bond linkage to DiP-PEG-carboxyl fluorescein linker, illustrating the capacity of the gels to covalently bond with image enhancement agents.

It has unexpectedly been discovered that cells encapsulated using these molecular monolayers are far superior to previous approaches that rely on bulk polymerization. This is due in part to the superior thickness control produced using the claimed layer-by-layer formation technique. In addition, although the exact mechanism has yet to be identified, it appears that the molecular monolayer coatings enable implanted cells to avoid rejection while also enabling the implanted cells to receive nutrient, eliminate waste and exchange oxygen. This is evident in FIGS. 2 and 3, which show that human and Lewis rat islets, respectively, coated using the techniques disclosed herein survived for more than eight (8) days after encapsulation with little to no cell deaths. In addition, layers formed by this method are superior to an equivalent layer-by-layer self-assembly via ionic interactions, because such ionically bonded coatings are not stable over the long term.

According to various other embodiments, the coatings can have a highly branched architectural design. Such coatings can be used to build protective coatings on cells, cell clusters, or other bioactive agents, in this way allowing enhanced control over the physical, chemical, and biological properties of the coating. In addition, the unique branched system provides for a high degree of surface presentation of agents, thereby providing a novel platform for the chemoselective presentation of a large amount of agents on the surface of the coating (which could be highly beneficial for targeting, labeling, or as a bioactive interface).

Coatings having a highly branched architectural design can be superior in that: (1) the thickness of the layers can be controlled on a nano-scale; (2) the interconnected layers can be covalently linked resulting in highly stable layers; (3) the multi-branched nature of the functionality can result in significant increases in the number of functional groups available per surface; and (4) the complimentary electrostatic charges of the two polymers can enhance the efficiency of the procedure and the uniformity of layer deposition.

The highly branched coating systems according to various embodiments can result in the efficient, convenient, and complete coatings on pancreatic islets of Langerhans with controllable capsule thickness, capsule properties, and functionalities helping realize the development of bioartificial pancreas for the treatment of diabetes. The highly branched coating systems can be useful for encapsulation of drugs or other loads, as well as the efficient targeting of these agents in vivo, given the high degree of surface functionality of these polymers, multiple tags may be easily presented on the surface of the capsule. Therefore, the highly branched coating systems can provide a high degree of targeting potential for the capsules that are coated.

Various embodiments rely on the combined use of current, as well as, dendritic and hyperbranched polymeric materials for the assembly of functional conformal coatings with dendritic-based architectures via the layer-by-layer film deposition technique.

The nanostructured functional conformal coatings can be deposited onto viable cells and cell clusters, in addition to other biological relevant surfaces with nanometer thickness control. The coatings can have a thickness within a range having a lower limit and/or an upper limit. The range can include or exclude the lower limit and/or the upper limit. The lower limit and/or upper limit can be selected from 0.01, 0.05, 0.1, 0.2, 0.3, 0.4, 0.5, 1, 2, 3, 4, 5, 10, 15, 20, 25, 50, 75, 100, 200, 300, 400, 500, 600, 700, 800, 900, 1000, 1100, 1200, 1300, 1400, 1500, 2000, 3000 nm. For example, according to certain preferred embodiments, the coatings can have a thickness from 0.01 nm to 1000 nm. Thickness range is dependent upon desired application.

Chemical functionalities that can be utilized to achieve the layer-by-layer surface film deposition with added functionality include, but are not limited to, Staudinger ligation, electrostatic interactions, native chemical ligation, Diels-Alder reaction, click chemistries, selective molecular recognition motifs, other non-specific chemical/physical interactions, and combinations thereof.

The functional conformal coatings have many uses, including, but not limited to, semipermeable physical membranes for the immunoisolation of cells and functionalization of cell surfaces for particular applications such as molecular recognition, control over biological processes, drug delivery, and labeling systems for imaging capabilities. Advantages of functional conformal coatings with dendritic-based architectures according to various embodiments include adequate polymer structural design for maximum control and efficiency over the layer-by-layer film deposition, substantial increase in the number of available end groups for chemical functionality, and manipulation of structural design of deposited films by changing the chemical and physical properties of the dendrimers and hyperbranched polymers.

The function and advantage of these and other embodiments of the present invention will be more fully understood from the examples described below. The following examples are intended to facilitate an understanding of the invention and to illustrate the benefits of the present invention, but are not intended to limit the scope of the invention.

EXAMPLES

Customized alginate and PEG (polyethylene glycol) polymers were fabricated to create a chemoselective ligation scheme between these polymers based on the Staudinger Ligation chemistry for cellular encapsulation and bioconjugation. As illustrated in the Schemes and Figures below, the azide-alginate [1] is cross-linked via PEG having either 2 or 4 DiP end groups ([2] or [3], respectively) to form macro-gels, micro-gels, or nano-scale layers. PEG linear linkers having an N-Hydroxysuccinimide (NHS) with an activated carboxylate group at one end and either a 1-methyl-2diphenylphosphphino-terephthalate (DiP) ([4]) or an azide ([5]) group at the other were fabricated for the nano-scale layering. Bioconjugation capacity was further demonstrated by fluorescently labeling one end of a PEG linear linker and having a DiP ([6]) or an azide ([7]) group at the other end. It was found that PEG linkers bearing a negative charge minimized phase separation and aggregation of the PEG polymer with alginate and may help with any polymer-related cell toxicity by possibly preventing diffusion of the polymers across biomembranes. The molecular weights of alginate, PEG, or alginate-PEG polymers were chosen for a particular application in order to control, viscosity of solution, permeability, cross-linking preincubation time, and nano-layering efficiency. These polymers may then be used for bioorthogonal encapsulation (via cross-linking) and functionalization of cells in macro-scale gels, microcapsules, or nano-scale layers systems.

Materials

Purity, functionalization, and characterization of the polymers were assessed using attenuated total reflectance Fourier transform infrared (ATR-FT-IR) spectroscopy, mass spectroscopy, and proton nuclear magnetic resonance ($^1$H-NMR) spectroscopy. ATR-FT-IR spectra were obtained using the PerkinElmer Spectrum 100 FT-IR spectrometer with the Universal ATR (1 bounce, Di/ZnSe) sampling accessory. UV-Vis spectra were obtained using the Molecular Devices SpectraMax M5 Microplate/Cuvette Reader. Samples were submitted to the University of Miami Chemistry Department for mass spectroscopy (VG Trio-2 FAB-MS or Bruker Bioflex IV MALDI-TOF-MS) and $^1$H-NMR (Bruker, 400 MHz) analysis. Samples were submitted to the North Carolina State University Mass Spectrometry Facility for ESI-TOF-MS analysis. Most chemical reagents were purchased from Sigma-Aldrich at the highest purity available or as indicated below.

Synthesis and Characterization of Alginate-PEG-N$_3$, Azide-Alg [1]

Ultra purified sodium alginate with high (>60%) guluronic acid content and high molecular weight (UP-MVG) from NovaMatrix (Pronova Biomedical, Norway) was used as the base polymer for azide functionalization and for control studies of standard alginate capsules. In addition, the very low viscosity sodium alginate (Pronova UP VLVG, NovaMatrix) was functionalized with azide groups and used as a lower molecular weight alternative for the studies.

H$_2$N-PEG-N$_3$ (M$_w$ of 372 g/mol by ESI-TOF-MS), the functional group added to [1], was fabricated via tosyl-PEG-tosyl and N$_3$-PEG-N$_3$ polymer precursors as shown in Scheme 1, below.

Scheme 1

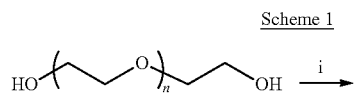

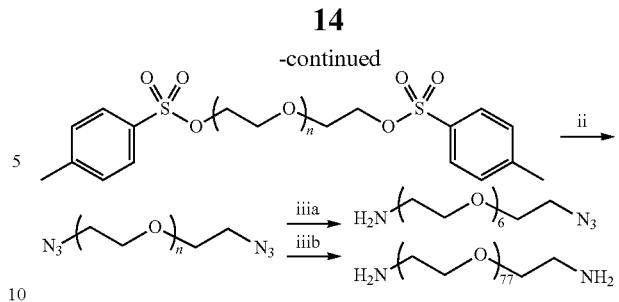

The catalysts and additional reactants used for Scheme 1 are as follows: (i) tosyl(Ts)Cl, 4-(dimethylamino)pyridine (DMAP), dichloromethane (DCM); (ii) NaN$_3$, N,N-dimethylformamide (DMF); (iiia) Ph$_3$P, HCl, H$_2$O, Et$_2$O, EtOAc; (iiib) Ph$_3$P, tetrahydrofuran (THF), water. Ts-PEG-Ts was prepared by tosylation (Ts) of both hydroxyl end groups of HO-PEG-OH (M$_w$ of 311 g/mol by ESI-TOF-MS). HO-PEG-OH (2.4 g) was dried by stirring under vacuum at 75° C. for 1 hr. After cooling to room temperature (RT, 21-22° C.), the dry PEG oil was dissolved in 3 mL anhydrous dichloromethane (DCM) followed by slow (within 10 min) addition of a freshly prepared solution of 3.94 g (20.46 mmol) p-toluenesulfonyl chloride and 2.80 g (22.69 mmol) 4-(dimethylamino)pyridine (DMAP) in 10 mL anhydrous DCM, followed by stirring at RT for 3 h. The resulting mixture was washed once with a 30 mL mixture of water/ice/1 mL HCl (36.8%) and once with 20 mL saturated NaHCO$_3$ solution containing some ice. The resulting organic layer was dried over anhydrous Na$_2$SO$_4$, filtered through a silica gel pad, and the solvent removed under reduced pressure. The resulting polymer, Ts-PEG-Ts (3.90 g), was added to NaN$_3$ (1.27 g), and 4 mL anhydrous N,N-dimethylformamide (DMF) and reacted for 4 h at 80° C. under Ar flow and for 15 h at RT (21-22° C.). Following incubation time, diethyl ether (20 mL) was added. Insoluble salts were removed by filtration through a 0.45 µm polypropylene filter, diethyl ether was removed under reduced pressure, and the DMF was removed by short-path distillation at 80° C. with help of Ar flow. The residue was dissolved in 20 mL diethyl ether and passed through a silica gel pad. The diethyl ether was removed under reduced pressure. The product, N$_3$-PEG-N$_3$ was dried first by Ar-flushing and then under reduced pressure. A solution of triphenylphosphine (Ph$_3$P) (1.06 g) in 9 mL of 50% (v/v) diethyl ether in ethyl acetate was slowly (within 1 h) added to a solution of N$_3$-PEG-N$_3$ (1.5 g), 50% (v/v) diethyl ether (4.5 mL) in ethyl acetate, and 0.5M HCl$_{aq}$ (9 mL) under Ar-flow and rapid stirring. Solution was then stirred for 19 h at RT. The aqueous phase was collected and made basic with addition of 6M NaOH$_{aq}$ (1.0 mL). The solution was then cooled in ice-water bath for 2 h while bubbling Ar, passed through a 0.45 µm polypropylene filter, and extracted 7 times with 3 mL dichloromethane (DCM). All combined DCM was dried over anhydrous Na$_2$SO$_4$, passed through a silica gel pad, and DCM removed under reduced pressure followed by Ar-flushing. Method as outlined resulted in 1.0 g of H$_2$N-PEG-N$_3$ Scheme 2, below, shows the fabrication of alginate-PEG-N$_3$ [1].

Scheme 2

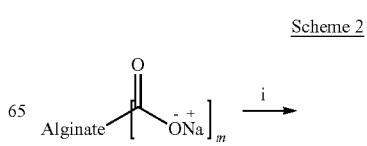

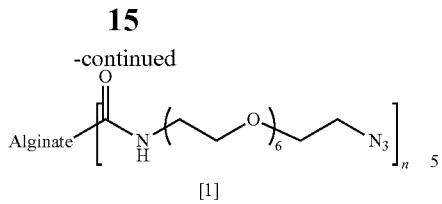

[1]

In scheme 2, the catalysts and additional reactants are as follows: (i) EDC, NHS, $NH_2$—PEG-$N_3$. In Scheme 2, sodium alginate (50 mg) (UP-MVG), N-hydroxysuccinimide (14 mg, 0.12 mmol), and 2-(N-morpholino)ethanesulfonic acid (62 mg, 0.29 mmol) were dissolved in 5 mL deionized water. A solution of $H_2N$-PEG-$N_3$ (28 mg, 0.08 mmol) in 200 µL $H_2O$ was added.

After stirring for 10 min at RT, 1-ethyl-(dimethylaminopropyl)carbodiimide hydrochloride (EDC) was added and stirring continued for 25 min at RT. The amount of EDC added varied from 56 mg to 167 mg, depending on the degree of functionalization (from 3 to 13% by $H^1$-NMR and ATR-FT-IR) desired. For this study, it was found that the addition of 116 mg of EDC resulted in high (9-12%) degree of $H_2N$-PEG-$N_3$ functionalization. This alginate was used for all encapsulation experiments in order to minimize possible EDC-related side reactions with alginate. Following incubation, 55 µL of 6 M NaOH was added and stirred for an additional 10 min. Purification was achieved by (at least) 4 days dialysis (10,000 MWCO membrane) against 600 mL water changed three times a day. During the first 3 days, 10 µL of 6M NaOH and 400 µL 4.26M NaCl was added twice daily to the alginate-containing solution and mixed. Finally, solution was filtered through a 0.45 µm membrane and lyophilized. The yield was 49 mg to 56 mg of a white, foamy, and solid material. The Kaiser test was negative. ATR-FT-IR: 3279, 2878, 2113, 1658 (shoulder), 1601, 1547 (shoulder) $cm^{-1}$. $^1H$-NMR ($D_2O$): δ 3.45-3.93 (s-m, 1H, PEG) and 4.67-4.95 (m; 5H or 2H for alginate with 3-5 or 10-13% modification, respectively).

The same above procedure was followed to synthesis Azide-Alginate having lower molecular weight alginate except that 50 mg of UP-VLVG alginate was used instead. For the fluorescent labeling of [1] (Azide-Alg-CF [1]), 20 mg of $H_2N$-PEG-CF (synthesized as part of compound [6] and [7]) was also mixed with the alginate prior to addition of EDC.

Synthesis of Poly(ethylene glycol) (PEG) Diphosphine, 2-DiP-PEG [2]

Scheme 3, below, shows a pathway for synthesis of Poly (ethylene glycol) (PEG) diphosphine, called 2-DiP-PEG.

Scheme 3

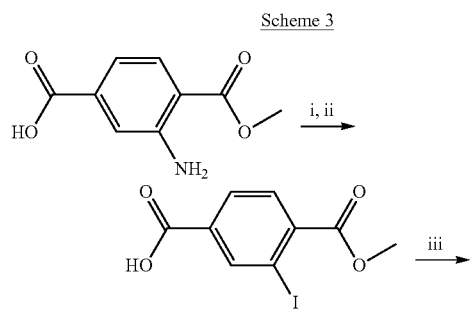

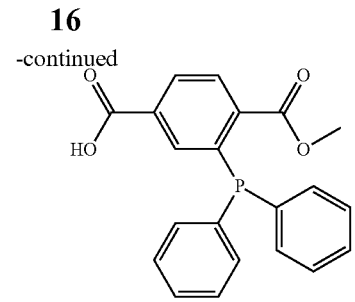

In Scheme 3, the catalysts and additional reactants are as follows: (i) HCl, $NaNO_2$; (ii) KI; (iii) $Pd(Ac)_2$, $Ph_2PH$, acetonitrile. Poly(ethylene glycol) (PEG) diphosphine, called 2-DiP-PEG [2] was fabricated from the starting PEG polymer of $NH_2$—PEG-$NH_2$ ($M_w$ of 3513 g/mol by MALDI-TOF-MS). Functionalization of the end units of the PEG was achieved by first fabricating the phosphine group or 1-methyl-2-diphenylphosphino-terephthalate (DiP), Scheme 3. DiP was fabricated by the addition of 1-Methyl-2-aminoterephthalate (1.0 g, 5.10 mmol) to 10 mL of cooled HCl and stirred 10 min. $NaNO_2$ (0.36 g, 5.22 mmol) in 2.3 mL water was injected slowly (within 5 min) through a sealed rubber septum into the HCl mixture while stirring (an orange gas formed). After 5 min, the mixture was removed from the ice-water bath and stirred 25 min at RT. The resulting mixture was passed through glass wool and 0.45 µm polypropylene (pp) membrane filter into a stirring solution of (8.6 g, 51.7 mmol) KI and 14 mL water (mixture turns dark red with red-black precipitate). After stirring for 1 h at RT, the solution was mixed with 40 mL DCM and 35 mL of 1.57 M (55.0 mmol) $Na_2SO_3$. The DCM phase was collected and washed once with 35 mL of 4.28M NaCl solution. The DCM phase was collect, dried over anhydrous $Na_2SO_4$, filtered (0.45 µm, pp membrane), and DCM removed under reduced pressure. The yellow solid residue was dissolved in 6 mL methanol and filtered (0.45 µm, pp membrane). The product was precipitated by adding 4 mL water, cooling 1 h in ice-water bath, and stirring. It was collected by filtration and freeze-dried overnight to yield 832.0 mg of a yellow solid powder of 1-methyl-2-iodoterephthalate. A flame dried/Ar-flushed Schlenk tube was loaded with 1-methyl-2-iodoterephthalate (750 mg, 2.4506 mmol), $Pd(Ac)_2$ (5.8 mg, 0.0256 mmol), anhydrous acetonitrile (7.5 mL), and N,N'-diisopropylethylamine (900 µL, 5.1465 mmol). The mixture was stirred until fully dissolved and degassed (freeze-pump-thaw method). Diphenylphosphine (430 µL, 2.4489 mmol) was injected (dropwise) into the acetonitrile solution under Ar flow (solution turned red and clear). The solution was refluxed for 4 h under Ar pressure (balloon), cooled to RT (or incubated overnight at RT), and concentrated under reduced pressure. The red solid-oily stick mass residue was dissolved in 50 mL DCM and washed once with 25 mL water and 25 mL 1M HCl. The DCM was removed under reduced pressure. The product was recovered by washing the red-yellow solid residue with 10 mL cold methanol, rinsed 5×2 mL cold methanol, and filtration. After drying under reduced pressure, 656.8 mg of a yellow solid powder of DiP (Mw of 364.09 g/mol by ESI-TOF-MS) was obtained. 2-DiP-PEG [2] as shown in Scheme 4 was formed by the addition of N,N'-diisopropylcarbodiimide (DIC) (22.524, 0.1440 mmol, DIC) to a solution of DiP (52.8 mg, 0.1449 mmol) and N-hydroxysuccinimide (17.2 mg, 0.1465 mmol) in 1.2 mL DMF (anhydrous, degassed with Ar). After stirring for 30 min at RT under Ar flow, $NH_2$—PEG-$NH_2$ (200 mg, 0.0597 mmol) was added, followed by 4-dimethylaminopyridine (14.8 mg, 0.1200 mmol) after 1 hr.

After 3 hrs, stirring at RT under Ar flow, the product was precipitated with 12 mL cold diethyl ether and collected by centrifugation at 0° C. It was "crystallized" once in 10 mL 200 proof ethanol (warm to 37° C. to dissolve, cool in ice-water bath to precipitate, collect precipitate by centrifugation at 0° C.). It was dissolved/precipitated/collected once with 0.5 mL DCM/12 mL cold diethyl ether/centrifugation at 0° C. and dried under reduced pressure. The yield was 212.0 mg of a white to light yellow solid powder. The Kaiser test was negative. $M_w$ of [2]: 4057 g/mol by MALDI-TOF-MS. $^1$H-NMR (CDCl$_3$): δ 3.45-3.84 (m, 393H), 6.80 (s, 2H), 7.28-7.38 (m, 22H), 7.80-7.82 (dt, 2H, J=2.0, 1.8, 8.2 Hz), and 8.06-8.09 (m, 2H).

Synthesis of 4-DiP-PEG [3]

Scheme 4 shows the synthesis of multi-functional PEG molecules for cross-linking of alginate via the Staudinger ligation reaction.

reacting H$_2$N-4arm-PEG (300 mg, 0.027 mmol), Fmoc-Asp (OtBu)-NHS (64 mg, 0.126 mmol), and N,N'-diisopropylethylamine (24 µL, 0.137 mmol) in 1.2 mL anhydrous DMF for 30 min at RT. Purification was achieved by precipitating with 10 mL cold (ice-water bath) Et$_2$O, "crystallizing" in 10 mL EtOH (37° C. to dissolve then cool in ice-water bath to precipitate), and washing with 10 mL cold Et$_2$O. All precipitates were collected by centrifugation (3500 rpm, 0° C., 5 min). The precipitate was dried under vacuum to yield 311.7 mg of [Fmoc-Asp(OtBu)]$_4$-PEG as a yellow-green to white solid powder. Kaiser test: negative. ATR-FT-IR: 3534, 3311, 2883, 1727, 1675, 1533, 1099, 762, 742 cm$^{-1}$. Second, [Fmoc-Asp(OtBu)]$_4$-PEG (270 mg, 0.022 mmol) was dissolved in 1.2 mL of 20% piperidine in DMF and reacted 30 min at RT. The product, [H$_2$N-Asp(OtBu)]$_4$-PEG, was precipitated with 10 mL cold (ice-water bath) Et$_2$O and collected by centrifugation (3500 rpm, 0° C., 5 min). It was then dissolved in 6 mL EtOH at 37° C. followed by addition of 2 mL Et$_2$O, cooling in ice-water bath to re-precipitate the product

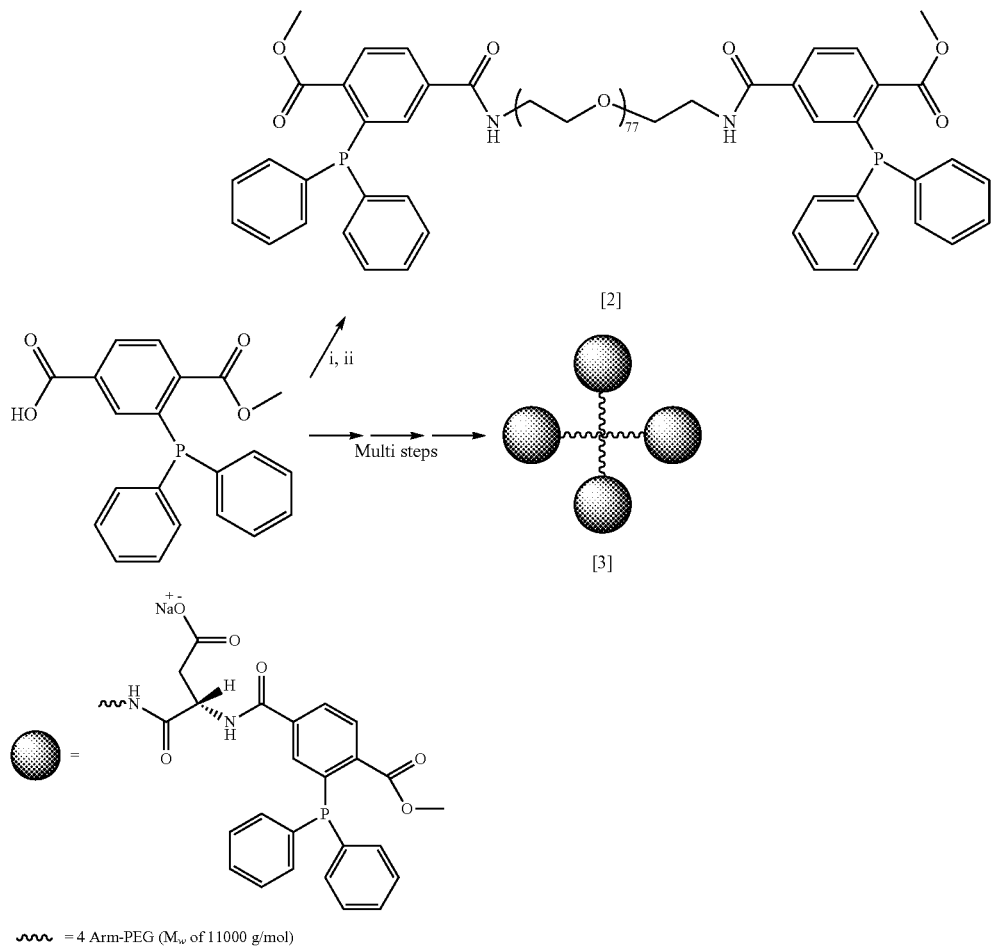

Scheme 4

= 4 Arm-PEG ($M_w$ of 11000 g/mol)

In Scheme 4, the catalysts and additional reactants are as follows: (i) N,N'-diisopropylcarbodiimide (DIC), NHS; (ii) NH$_2$—PEG-NH$_2$, DMAP. All amino end groups of a 4arm-PEG ($M_w$ of 11,000 g/mol) were functionalized with aspartic acid (Asp) followed by DiP resulting in a negatively charged polymer bearing four reactive sites for efficient cross-linking or layering, Scheme 4. 4DiP-PEG [3] was synthesized by first and collected by centrifugation as above. It was washed with 10 mL cold Et$_2$O and dried under vacuum to yield 217.4 mg of a green to white solid powder. Kaiser test: positive. ATR-FT-IR: 3523, 3384, 2885, 1725, 1670, 1520, 1098 cm$^{-1}$. Third, [H$_2$N-Asp(OtBu)]$_4$-PEG (165 mg, 0.014 mmol), DiP-NHS (34 mg, 0.093 mmol), DMAP (7 mg), triethylamine (32 µL, 0.23 mmol), and 700 µL anhydrous DMF were reacted 23 h at RT. The product, [DiP-Asp(OtBu)]$_4$-PEG, was purified as in the second step above. To yield 165.7 mg of a green to white solid powder. Kaiser test: negative. ATR-FT-IR: 3508, 3324, 2883, 1721, 1665, 1533, 1101, 748, 699 cm$^{-1}$. Finally, [DiP-Asp(OtBu)]$_4$-PEG (145 mg, 0.011 mmol) was reacted in a DCM solution containing 5% (v/v) triisopropylsilane and 35% (v/v) trifluoroacetic acid for 3 h at RT. The polymer was precipitated and washed once with 10 mL cold Et$_2$O followed by drying under vacuum. The dried product was dissolved in 400 µL DMF containing 37 µL of triethylamine and stirred well. Cold Et$_2$O (10 mL) was added to precipitate the polymer, which was then dissolved in 6 mL EtOH at 37° C. and cooled in ice-water bath to re-precipitate. The precipitate was washed once with 10 mL cold Et$_2$O and dried under vacuum.

at 37° C. and precipitated by cooling in ice-water bath), washed with 10 mL Et$_2$O, and dried under vacuum. Yield: 187 mg of a white, solid powder. Kaiser test: negative. ATR-FT-IR: 2884, 1656, 1101, 1538, 749, 699 cm$^{-1}$. Second, 180 mg of DiP-PEG-COOH was reacted with 15.8 mg NHS and 21.1 µL diisopropylcarbodiimide in 700 µL anhydrous DMF for 3 h under Ar. The product was collected and purified as in the first step except that crystallization was performed only once. This activation reaction was repeated once more. Yield: 155 mg of a white, solid powder. ATR-FT-IR: 2884, 1812, 1783, 1738, 1660, 1102, 1543, 750, 700 cm$^{-1}$.

Synthesis of Azide-PEG-NHS 151

The structure of Azide-PEG-NHS [5] is shown below.

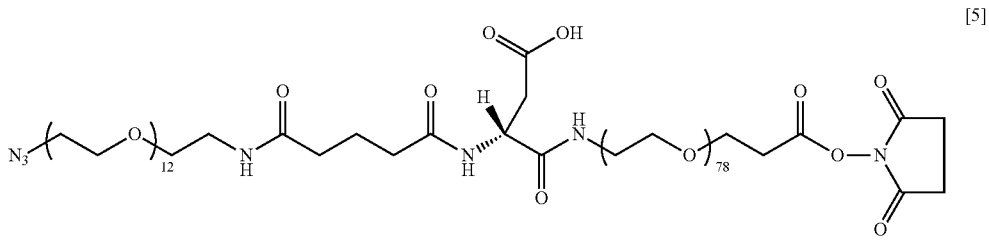

The resulting polymer was dissolved in 1 mL water and passed through a 4 mL column of SP-Sephadex C-25 using water as solvent and freeze-dried to yield 123.3 mg of [DiP-Asp(Na$^+$)]$_4$-PEG or [3], a green-white solid powder. ATR-FT-IR: 3511, 2883, 1720, 1658, 1589, 1537, 1095, 749, 699 cm$^{-1}$.

This polymer was also prepared as above but without Asp (aspartic acid) for comparison.

Synthesis of DiP-PEG-NHS [4]

The structure of DiP-PEG-NHS [4] is shown below.

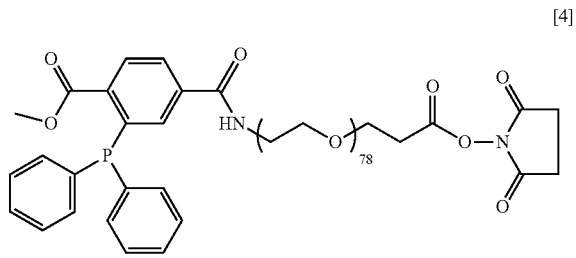

It was prepared in two steps process. First, the DiP-NHS (26.8 mg) was reacted with H$_2$N-PEG-COOH (200 mg, from Laysan Bio, M$_w$ 3400 g/mol) and triethylamine (31.8 µL) in 800 µL anhydrous DMF for 3 h at room temperature (RT) under Ar. The resulting polymer, DiP-PEG-COOH, was collected by precipitation with 10 mL cold (ice-water bath) Et$_2$O and collected by centrifugation (3500 rpm, 5 min, 0° C.). It was then "crystallized" three times in 8 mL EtOH (dissolved The synthesis of Azide-PEG-NHS consisted of five steps: (1) H$_2$N-PEG-COOH (300 mg, Laysan Bio, M$_w$ 3400 g/mol) was reacted with 50 mg Fmoc-Asp(OtBu)-NHS and 19 µL N,N'-diisopropylethylamine in 1 mL anhydrous DMF for 30 min at RT under Ar. Cold Et$_2$O (10 mL) was added with vortex to precipitate the product, which was collected by centrifugation. It was dissolved in 6 mL EtOH at 37° C. and re-precipitate by cooling in ice-water bath. After washing with 10 mL Et$_2$O, it was dried under vacuum. Yield: 315 mg of a white, solid powder. Kaiser test: negative. ATR-FT-IR: 3516, 3317, 2884, 1727, 1668, 1539, 1101, 762, 743 cm$^{-1}$. (2) Product from step 1 (290 mg) was reacted with 1.2 mL of 20% piperidine in DMF for 30 min. Purification was achieved as in step 1 with the addition that the dried powder was dissolved in 1 mL water, passed through a 4 mL SP-Sephadex C-25 column using water and freeze-dried. Yield: 270 mg of a white, solid powder. Kaiser test: positive. ATR-FT-IR: 3505, 3330, 2884, 1725, 1659, 1550, 1100 cm$^{-1}$. (3) Product from step 2 (250 mg) was reacted with 70 mg of azide-PEG-NHS (M$_w$ 835 g/mol), 3 mg N,N'-dimethylaminopyridine, and 39 µL triethylamine in 700 µl DMF for 23 h at RT under Ar. Product was collected and purified as in step 1. Yield: 248 mg of a white, solid powder. Kaiser test: negative. ATR-FT-IR 3519, 3311, 2884, 2105, 1729, 1654, 1545, 1100 cm$^{-1}$. (4) Product from step 3 (230 mg) was reacted with 18 mg NHS and 24 µL of diisopropylcarbodiimide in 600 µL DMF for 2 h at RT under Ar. This activation step was repeated once more. The product was collected and purified as in step 1. Yield: 208 mg of a white, solid powder. ATR-FT-IR: 3516, 3320, 2885, 2107, 1812, 1782, 1737, 1658, 1545, 1100 cm$^{-1}$. (5) Product from step 4 (190 mg) was reacted with 1 mL of DCM solution containing 5% v/v triisopropylsilane and 35° A) v/v trifluoroacetic acid for 3 h at RT under Ar. Product was collected and purified as in step 1. Yield: 172 mg of a white solid powder. ATR-FT-IR: 3524, 3319, 2885, 2105, 1812, 1783, 1737, 1659, 1543, 1100 cm$^{-1}$.

Synthesis of DiP-PEG-CF [6]

The structure of DiP-PEG-CF [6] is shown below.

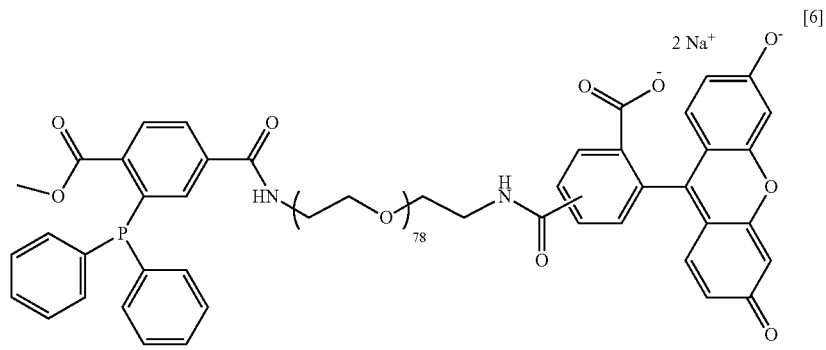

The synthesis of DiP-PEG-carboxyfluorescein(CF) consisted of two main steps: (1) H$_2$N-PEG-NH$_2$ (200 mg, M$_w$ 3513 g/mol) was reacted with 5(6)-carboxyfluorescein-NHS (28 mg, M$_w$ 473.39) and triethylamine (15.9 µL) in 1 mL anhydrous DMF for 20 min at RT under Ar in the dark. Cold (ice-water bath) Et$_2$O (10 mL) was added to precipitate the polymer and was collected by centrifugation (3500 rpm, 5 min, 0° C.). The precipitate was dissolved in 8 mL EtOH with vortex at 37° C. followed by cooling in ice-water bath to re-precipitate and centrifuged as above to collect the precipitate. After washing the precipitate with 10 mL cold Et$_2$O, it was dried under reduced pressure. The dry polymer was dissolved in 1.5 mL water and passed through an 8 mL column of SP-Sephadex C-25 followed by freeze-drying. This last purification step was repeated but using a QAE Sephadex column instead. Finally, it was dissolved in 3 mL DCM filtered through a 0.45 µm membrane filter, precipitated with 20 mL cold Et$_2$O, and dried under reduced pressure. Yield: 107 mg of a yellow-orange, solid powder. Kaiser test: positive. ATR-FT-IR: 2884, 1658, 1615, 1546, 1100 cm$^{-1}$. (2) Product from step 1 (70 mg) was reacted with 9 mg of DiP-NHS and 10.4 µL triethylamine in 280 µL anhydrous DMF for 2 h at RT under Ar. Cold Et$_2$O (5 mL) was added to precipitate the product. It was dissolved in 5 mL EtOH at 37° C., cooled in ice-water bath to precipitate, collected by centrifugation as above, washed with Et$_2$O, and dried under reduced pressure. The dry polymer was dissolved in 1 mL water, passed through a 3 mL SP-Sephadex C-25 column using water as solvent, freeze-dried, dissolved in 5 mL EtOH at 37° C., filtered through a 0.45 µm membrane filter, cooled in ice-water bath to precipitate, washed with 5 mL cold Et$_2$O, and dried under reduced pressure. Yield: 63 mg of an orange solid powder. Kaiser test: negative. ATR-FT-IR: 2885, 1758, 1721, 1656, 1613, 1548, 1099, 750, 699 cm$^{-1}$. M$_w$: 3982 g/mol by MALDI-MS.

Synthesis of Azide-PEG-CF [7]

The structure of Azide-PEG-CF [7] is shown below.

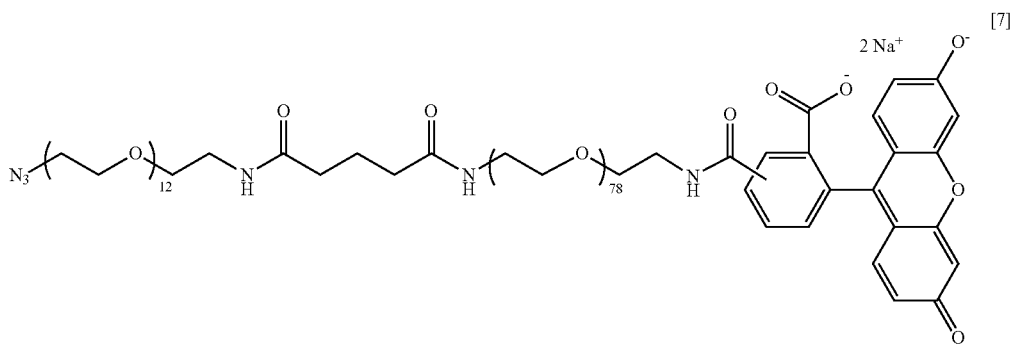

The synthesis of Azied-PEG-CF consisted of two main steps: (1) The same step 1 as described for compound [6]. (2) The product from step 1 (90 mg) was reacted with 19.2 µL N$_3$-PEG-NHS (M$_w$ 835 g/mol) and 12.8 µL triethylamine in 350 µL anhydrous DMF for 30 min at RT under Ar in the dark. The product was purified as described in step 2 for compound [6]. Yield: 93 mg of an orange, solid powder. Kaiser test: negative. ATR-FT-IR: 2883, 2099, 1656, 1611, 1572, 1546, 1097 cm$^{-1}$.

Microcapsule Formation and Cellular Encapsulation

Cross-linked Alginate-PEG (XAlg-PEG) microbeads were fabricated using a modification of the protocol originally developed by Sun (1). XAlg-PEG gels consisted of 2.5 wt % Azide-Alg [1] and 4.75 wt % 2-DiP-PEG [2]. The solution of [1] and [2] were generated by first dissolving 3.1 wt % of M in saline in one vial and 23.75 wt % of [2] in another. Following complete dissolution of the polymers in saline, the solutions were mixed in a 1:1.9 ratio. The mixture of [1] and [2] were gently mixed for 1 hr 15 mins prior to microbead fabrication. Microbeads were prepared via needle extrusion of the XAlg-PEG solution into a gelling basin of 50 mM BaCl$_2$ (Sigma Aldrich) and 0.025% (v/v) Tween 20 (Sigma Aldrich) solution. The size of the droplets was controlled by a parallel airflow generator (10 kPa pressure of air with a 1 in distance from the needle to the gelling solution) and the manual force applied to the syringe. The beads were exposed to the gelation solution for 5 min, aspirated, and then rinsed with phosphate-buffered solution (PBS) three times to remove excess barium. For microcapsules containing cells, cells were mixed in either polymer solution immediately prior to needle extrusion. Following the homogeneous distribution of the cells within either the XAlg-PEG solutions, the cell/polymer suspension was extruded through the microencapsulation generator and microbeads were fabricated. Following a 5 min exposure to the barium gelation solution and PBS rinse, the cell-containing microbeads were washed in the appropriate culture media for the cell type.

FIGS. 1-4 show microcapsules used for encapsulating cell lines and islets as disclosed herein. In FIG. 1, light lines represent Azide-Alg molecules [1] and the darker lines represent the 2-Dip-PEG molecules [2]. Covalent linkages can be established in pre-incubation time, followed by the exposure to barium ions during capsules formation to form a gel instantaneously. After ionic gel formation, covalent cross-linking between the two reactive polymers continues to "lock" the gel in place.

FIGS. 2(a)-(c) show confocal images of Lewis rat islets encapsulated as disclosed herein stained such that live cells are green whereas dead cells are red. FIGS. 2(A), (B) and (C) show the Lewis rat islets on post-encapsulation Day 1, Day 5, and Day 8, respectively.

FIGS. 2(a)-(c) show confocal images of human islets encapsulated as disclosed herein stained such that live cells are green whereas dead cells are red. FIGS. 2(A), (B) and (C) show the human islets on post-encapsulation Day 1, Day 5, and Day 8, respectively.

Figure 5:
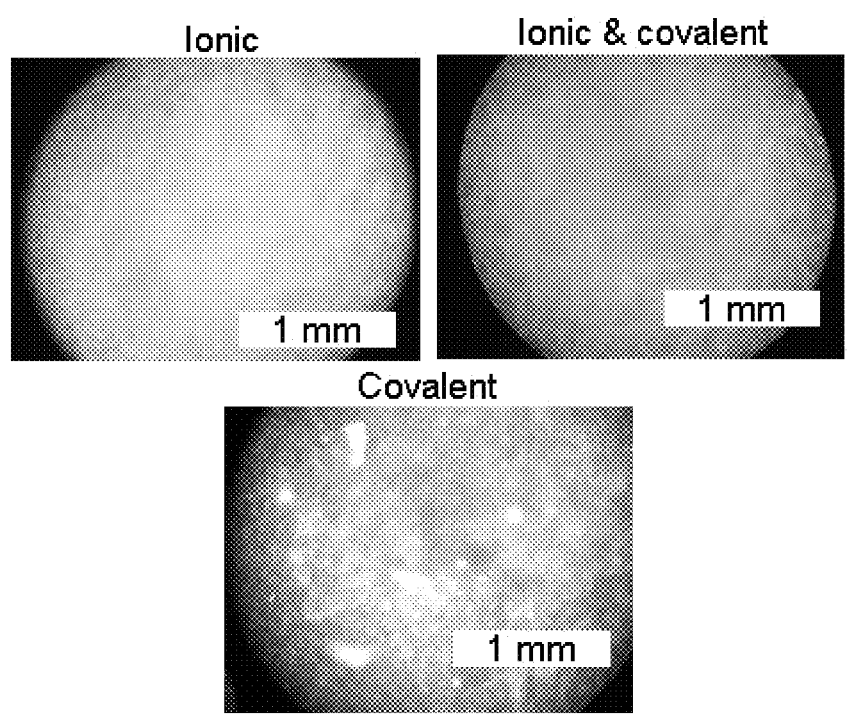
FIGS. 5(A)-(C) show beads prepared with 1.5 wt % of molecule [1] and molecule [3] via (A) ionic bonding (with $Ba^{2+}$ and no molecule [3]), (B) both ionic and covalent bonding, and (C) covalent bonding (after removal of $Ba^{2+}$ with EDTA).

In addition, ionic (Ba$^{2+}$), ionic/covalent, and covalent crosslinked beads were also prepared with [1] and [3] utilizing only 1.5 wt % of both polymers (FIG. 5). For the covalent cross-linking, a pre-incubation period of only 45 min was utilized. An advantage of compound [3] is more soluble polymeric mixtures. It is envisioned that the pre-incubation time can be eliminated (if needed) by designing higher molecular weight polymers (PEG or alginate/PEG) bearing the phosphine groups for the Staudinger ligation.

Nano-Scale Layer Fabrication and Cellular Encapsulation

Nano-scale layers were fabricated on glass microcarrier beads of size ranging from 150 to 210 µm. The beads were cleaned with piranha solution (mixture of 3:1 concentrate sulfuric acid and hydrogen peroxide) for 20 minutes and then washed extensively with DI water. The glass beads were then amino functionalized by a 5% wt solution of 4-aminobutyl-triethoxy-silane in toluene at 80° C. for 5 hours to mimic the amino groups on the cell surface. Amino functionalized glass beads were incubated in a 0.5 to 5 mM solution of Azide-PEG-NHS [5] for 1 hour to initiate the first layer of poly (ethylene glycol). Following the PEG coating, the beads were washed to remove the non-specific adsorbed polymer and incubated again in a 0.7 mM solution of 4-DiP-PEG [3] for 45 minutes to form a second layer of multi-arm PEG. After washing the beads, they were incubated again in a 0.2 to 2 mM of Azide-Alg [1] or fluorescent labeled Azide-Alg-CF [1a] for 1 to 2 hours to form a third layer of polymer. Additional layers are added by alternating the 4-DiP-PEG [3] and Azide-Alg [1] or Azide-Alg-CF [1a]. A nanocapsule was also made by incubating the amino functionalized glass beads with Azide-PEG-NHS [5] and then in a mixture of 4-DiP-PEG [3] and Azide-Alg [1] or Azide-Alg-CF [1a] (0.7 and 0.2 mM respectively for 2 hrs) to form a multilayer capsule.

Figure 6:
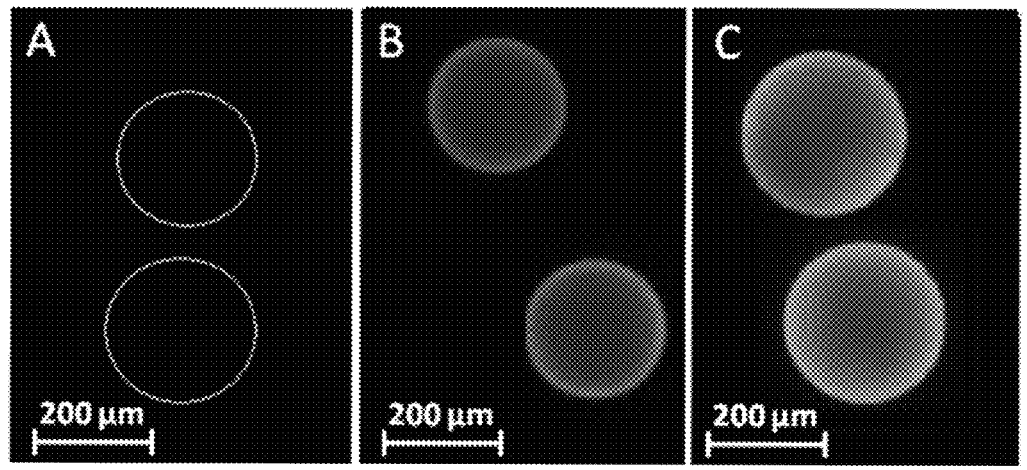
FIGS. 6(A)-(C) show fluorescent microscope images of glass microcarrier beads functionalized with 4-aminobutyl-triethoxy-silane and reacted with functionalized polymers.

FIG. 6(A) shows fluorescent microscope image of amino functionalized glass microcarrier beads following incubation with NHS-PEG-CH$_3$ (Laysan Bio, M$_w$ 5,000 g/mol) (2.5 mM, 1 hr), rinse with Dulbecco modified phosphate buffer saline (DPBS) 1× buffer, subsequent incubation with 4-DiP-PEG [3] (0.7 mM, 45 minutes), another rinse, and final incubation of Azide-Alg-CF [1a] (0.2 mM and 2 hrs) and a rinse with buffer were performed. The lack of fluorescent on the glass beads surface is due to the absence 4-Dip-PEG and azide-Alginate-CF layer (Control experiment).

FIG. 6(B) shows fluorescent images of amino functionalized glass microcarrier beads following incubation with Azide-PEG-NHS [5] (2.5 mM, 1 hr), rinse, subsequent incubation with 4-DiP-PEG [3] (0.7 mM, 45 minutes), another rinse, and final incubation of Azide-Alg-CF [1a] (0.2 mM and 2 hrs) and final rinse with buffer. The third layer of polymer was labeled with FITC and all the layers are all covalent bond and stable even after five weeks in buffer solution.

FIG. 6(C) shows fluorescent images of amino functionalized glass microcarrier beads following incubation with Azide-PEG-NHS [5] (2.5 mM, 1 hr), rinse, subsequent incubation with a mixture of 4-DiP-PEG [3] and Azide-Alg-CF [1a] (0.7 mM and 0.2 mM, 2 hrs) and a final rinse with buffer.

FIGS. 7(A)-(F) show confocal fluorescent and light transmission images of nano-layering on glass microcarrier beads (170 to 210 µm glass beads were functionalized with 4-aminobutyl-triethoxy-silane) reacted with functionalized polymers.

Figure 7:
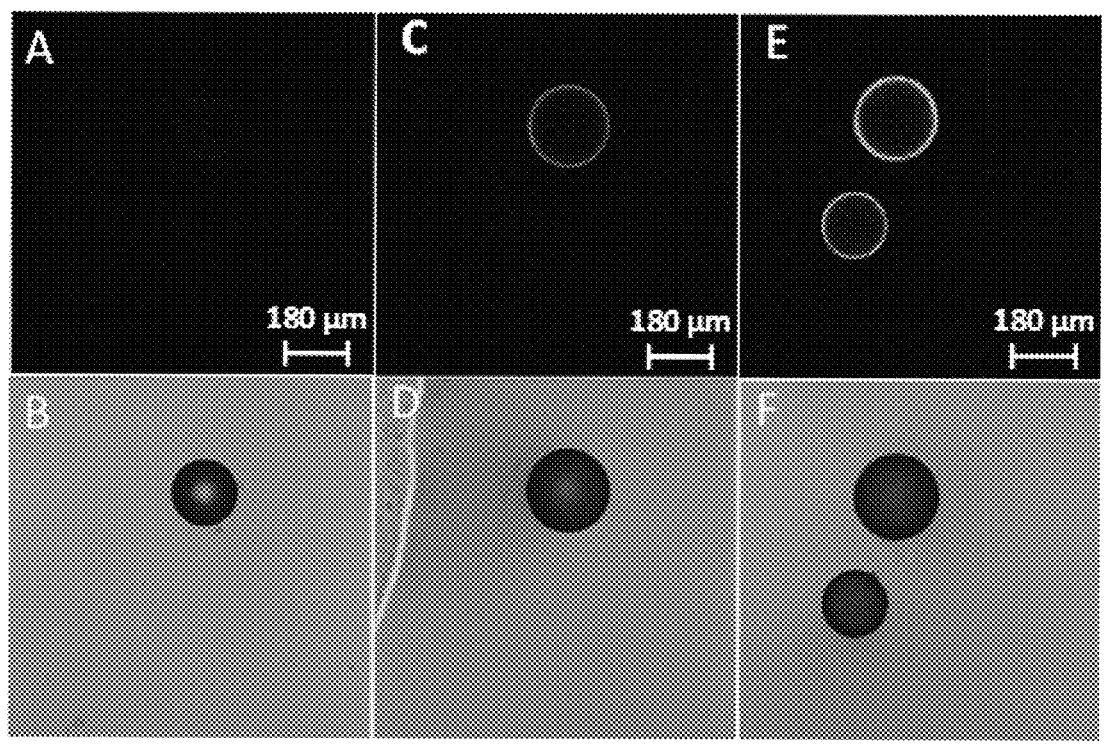
FIGS. 7(A)-(F) show confocal fluorescent and light transmission images of nano-layering on glass microcarrier beads (170 to 210 μm glass beads were functionalized with 4-aminobutyl-triethoxy-silane) reacted with functionalized polymers.
Figure 8:
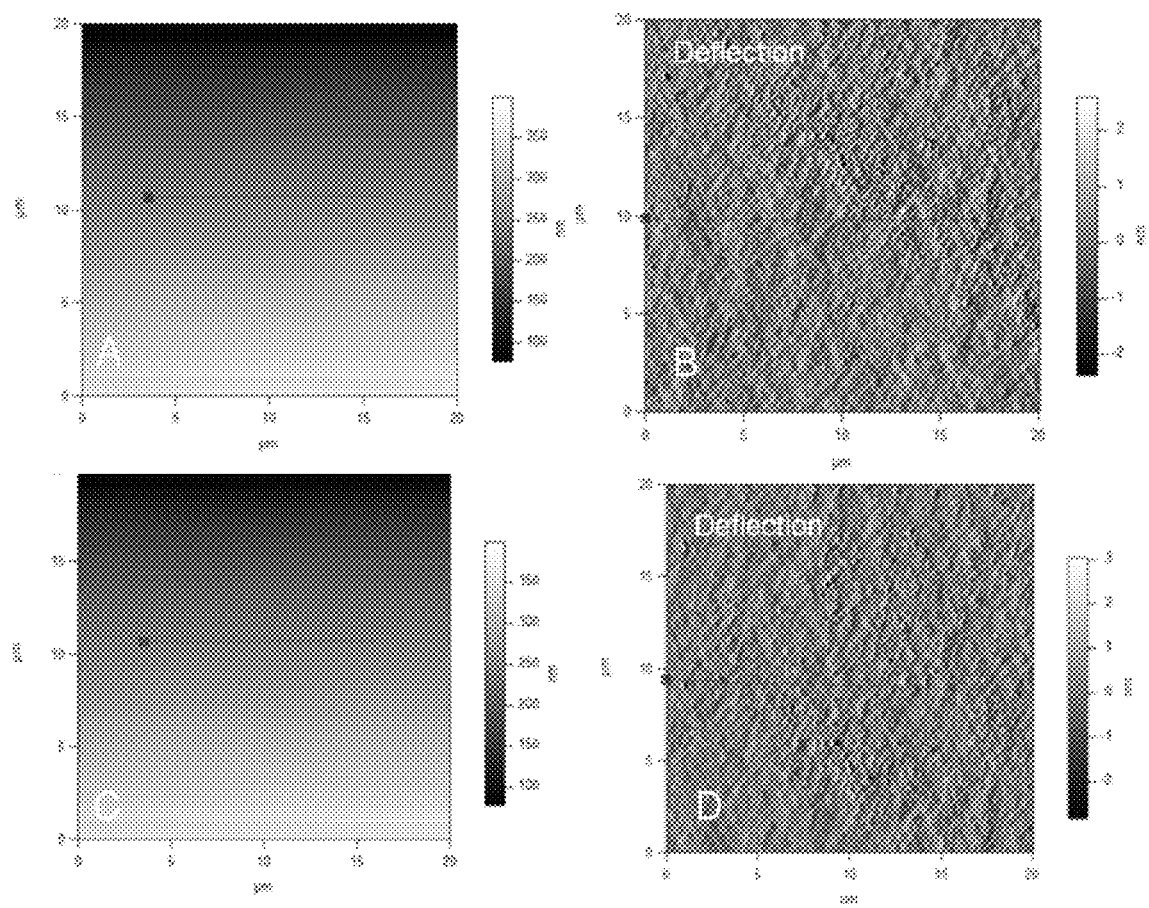
FIGS. 8(A)-(D) show Atomic Force Microscopy (AFM) images, where FIGS. 8(A) and (B) are height and deflection images, respectively, of Corning amino glass functionalized with a layer of Azide-PEG-NHS [5]

FIGS. 7(A) and (B) show confocal images, fluorescent and light transmission, respectively, of amino functionalized glass microcarrier beads following incubation with NHS-PEG-CH$_3$ (2.5 mM, 1 hr), rinsed with buffer and subsequent incubation with 4-DiP-PEG [3] (0.7 mM, 45 minutes) and wash and final incubation of Azide-Alg-CF [1a](0.2 mM and 2 hrs) and a final rinse with buffer. The lack of Azide-Alg-CF bounded to the glass surface is due to the absence of the 4-DiP-PEG and Azide-Alg-CF polymer (Control experiment)

FIGS. 7(C) and (D) show confocal images, fluorescent and light transmission, respectively, of amino functionalized glass microcarrier beads following incubation with Azide-PEG-NHS [5] (2.5 mM, 1 hr), followed with intensively rinsing with buffer. A Subsequent incubation with 4-DiP-PEG [3] (0.7 mM, 45 minutes), rinsing and final incubation of Azide-Alg-CF [1a] (0.2 mM and 2 hrs), and final rinsed with buffer was formed. The third layer of polymer was labeled with FITC which is stable and covalent bounded to the surface after five weeks in buffer.

FIGS. 7(E) and (F) show confocal images, fluorescent and light transmission, respectively, of amino functionalized glass microcarrier beads following incubation with Azide-PEG-NHS [5](2.5 mM, 1 hr), followed by rinsing with buffer and a subsequent incubation with a mixture of 4-DiP-PEG [3] and Azide-Alg-CF [1a] (0.7 mM, 0.2 mM, 2 hrs) and a final rinse with buffer. Multiple layers are formed after mixing the functionalized beads with 4-DiP-PEG [3] and Azide-Alg-CF [1a], resulting in a much thicker coating.

The morphology of each layer was studied by Atomic Force Microscopy (AFM). The nano-scale layers were prepared on a Corning amino glass slide following the same procedure for the nano-scale layer fabrication. Figures (A) and (B) are height and deflection images, respectively, of Corning amino glass functionalized with a layer of Azide-PEG-NHS [5]; while Figures (C) and (D) are height and deflection images, respectively, of Corning amino glass functionalized with a layer of Azide-PEG-NHS [5] followed by a layer of 4-DiP-PEG [3]. As shown in FIGS. 8(A)-(D), the surface morphology was found to be smooth, with no holes or de-wetting observed.

Cells are incubated in a 4 mM solution of NHS-PEG-DiP for 30 mins to initiate first layer of poly(ethylene)glycol. Following PEG coating, cells are then incubated with 0.5% Azide-Alg [1] for 1 hr and washed. After alginate coating, cells are then incubated with 2-DiP-PEG [2] for 1 hr. Additional layers may be added by alternating layers of Azide-Alg [1] and 2-DiP-PEG [2] (or 4-DiP-PEG [3]) with washes in between each polymer coating step.

FIGS. 9 and 10 show schematics of monolayer coating schemes. FIG. 9 shows a schematic representation of covalently linked layers of triarylphosphine PEG active ester (base layer), azido-alginate(interconnecting layer) and bi-triarylphosphine PEG (interconnecting layer and terminal layer).

FIG. 10 shows a hemical scheme outlining the reactions for the covalent linking of two layers (triarylphosphine PEG active ester and azido-alginate) on the islet surface. Alternatively, the azide group can be first linked to islet surface using compound [5] followed by alternate layers of compounds [3] and [1], image not shown.

Figure 11:
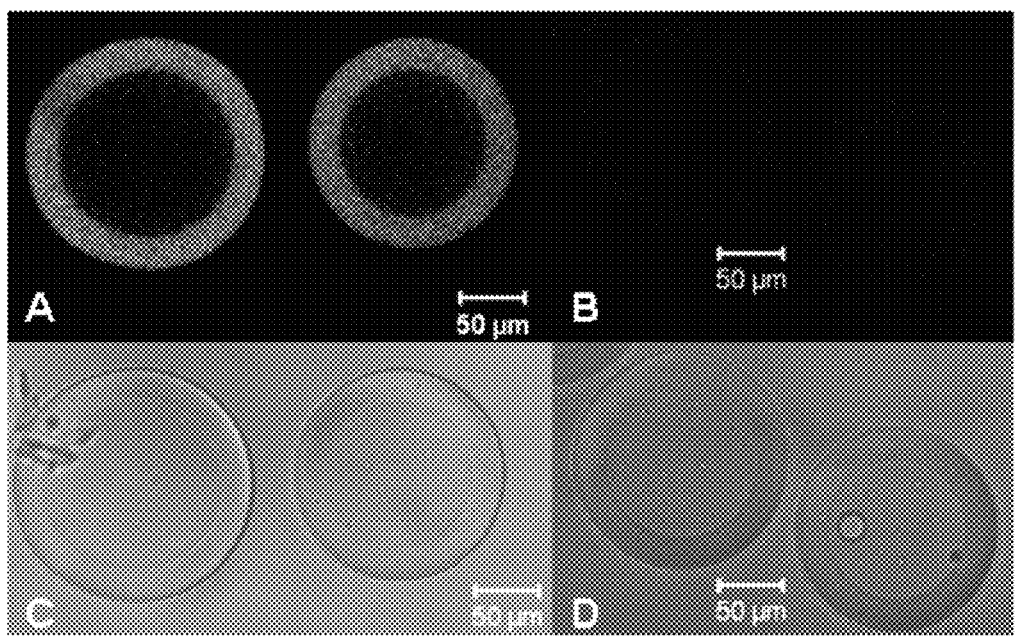
FIGS. 11(A)-(D) show fluorescent and light transmission confocal images of Cytodex-3 beads treated with functionalized polymers disclosed herein.

FIGS. 11(A)-(D) show confocal images of Cytodex-3 beads (dextran beads coated with a ~20-30 µm layer of denatured collagen) treated with functionalized polymers. FIGS. 11(A) and (C) are fluorescent and light transmission images, respectively, of collagen beads following incubation with DiP-PEG-NHS [4] (2.5 mM, 30 mins) and azide-PEG-CF [7] label (2.5 mM, 2 hrs). FIGS. 11(B) and (D) are fluorescent and light transmission images, respectively, of collagen beads following incubation with PEG-NHS (2.5 mM, 30 mins) and azide-PEG-CF label (2.5 mM, 2 hrs). Images illustrate selectivity of azide-PEG-CF reaction to triarylphosphine PEG and intensity of binding. The thick scale of the coating is due to the thickness of the collagen layer on the dextran beads, which is approximately 20-30 µm thick, where the active ester of the PEG polymers conjugates with the free amines throughout the layer.

Figure 12:
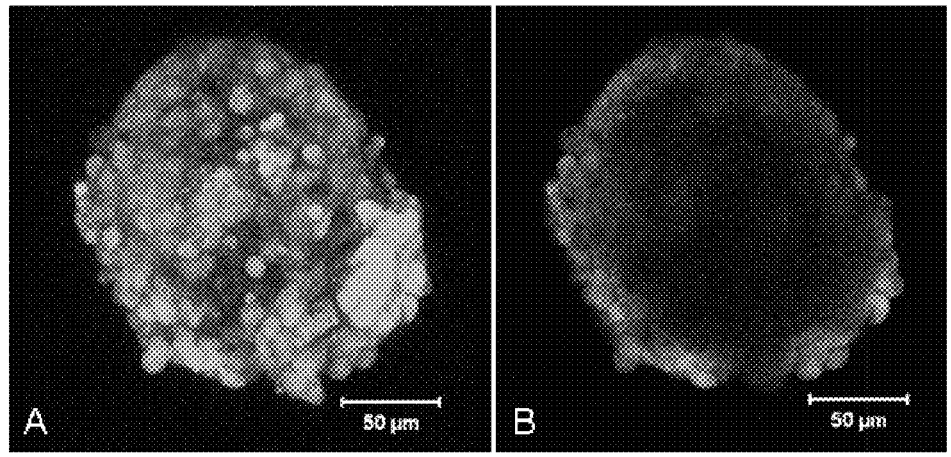
FIGS. 12(A) and (B) show confocal images of human islets treated with functionalized polymers as disclosed herein.

FIGS. 12(A) and (B) show confocal images of human islets treated with the functionalized polymers disclosed herein. Fluorescent confocal images of human islets following incubation with triarylphosphine PEG active ester [4] (2.5 mM, 30 mins) and azide-PEG-CF [7] label (2.5 mM, 2 hrs), where FIG. 12(A) is the projection of a z-stack image for the top half of the islet and FIG. 12(B) is an image of a single slice through the mid-section of the islet. Islets incubated with PEG active ester (2.5 mM, 30 mins) and azide-PEG-CF labels (2.5 mM, 2 hrs) did not exhibit fluorescence. Presumably, this is because the absence of the triarylphosphine on the PEG polymer prevented CF binding.

Macro-Scale Gel Formation.

Figure 13:
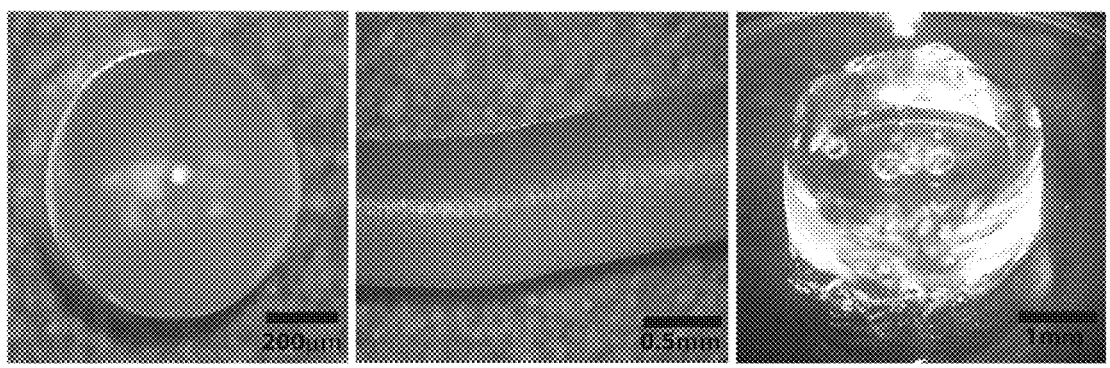
FIG. 13 shows various three-dimensional gels, capsules, cylinders, and disks, created using bulk cross-linking methods disclosed herein.

XAlg-PEG gels consisted of 2.50 wt % Azide-Alg [1] and 2.5-4.75 wt % 2-DiP-PEG [2] (or 4-DiP-PEG [3]). The solution of [1] and [2] were generated by first dissolving 3.1 wt % of [1] in saline in one vial and 23.75 wt % of [2] in another. Following complete dissolution of the polymers in saline, the solutions were mixed in a 1:1.0-1.9 ratio and mixed with cells. Gels were poured into molds or extruded through tubing and incubated for 5 hrs or until complete gel formation. The resulting gels could not be dissolved in EDTA and showed minimal swelling in various ionic solutions. FIG. 13 shows images of macro-scale gels produced as described above in the form of capsules, cylinders and disks.

Formation of a Highly Branched Coating System

A dendritic-based coating was accomplished by a combination of poly(amido amine) (PAMAM) dendrimer and novel hyperbranched alginate functionalized with complementary end groups for Staudinger ligation, which is a highly chemoselective and hence desirable covalent ligation scheme for cellular work. To prepare these materials, PAMAM of generation 5 was utilized to introduce one of the layers. Based on its dendritic structure, this PAMAM has 128 primary amino end groups available for reaction that were readily reacted with 1-methyl 4-pentafluorophenyl diester (MDT) in dichloromethane for 15-60 min. After purification by dissolution and precipitation using 50% methanol in dichloromethane and diethyl ether, the product was purified by dialysis and freeze dried. Glutaric anhydride was used to manipulate the net surface charge of PAMAM dendrimer in the presence of triethylamine base. PAMAM dendrimers having 15-40% of the end groups modified with MDT and surface net charge ranging from +110 to −38 were prepared and characterized by infrared and proton nuclear magnetic resonance (NMR) spectroscopies. For the other alternate complimentary polymer layer, hyperbranched alginate functionalized with azido (N3) end groups was prepared. Carbodiimide condensation of 3,5-dicarboxyphenyl glycineamide in the presence of alginate was utilized to grow the hyperbranches on the alginate polymeric backbone, followed by dissolution and precipitation in aqueous solution and acetone for purification and drying under reduced pressure. Due to free carboxylate end groups, the hyperbranched alginate is negatively charged. These carboxylate groups were utilized to functionalize the polymer with azido end groups via poly (ethylene glycol) linkers and characterized by infrared and proton NMR spectroscopies.

Figure 14A:
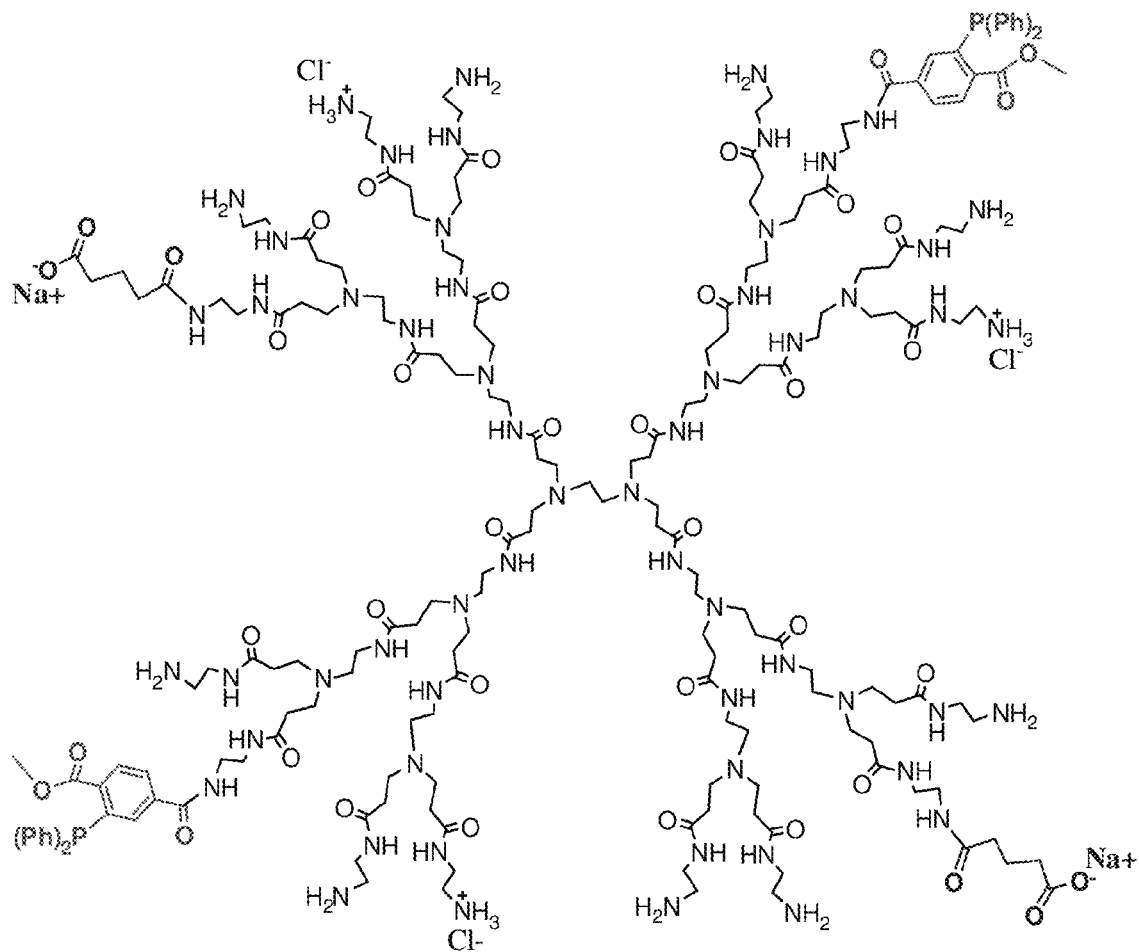
FIG. 14A is a diagram of a functionalized PAMAM dendrimer.
Figure 14B:
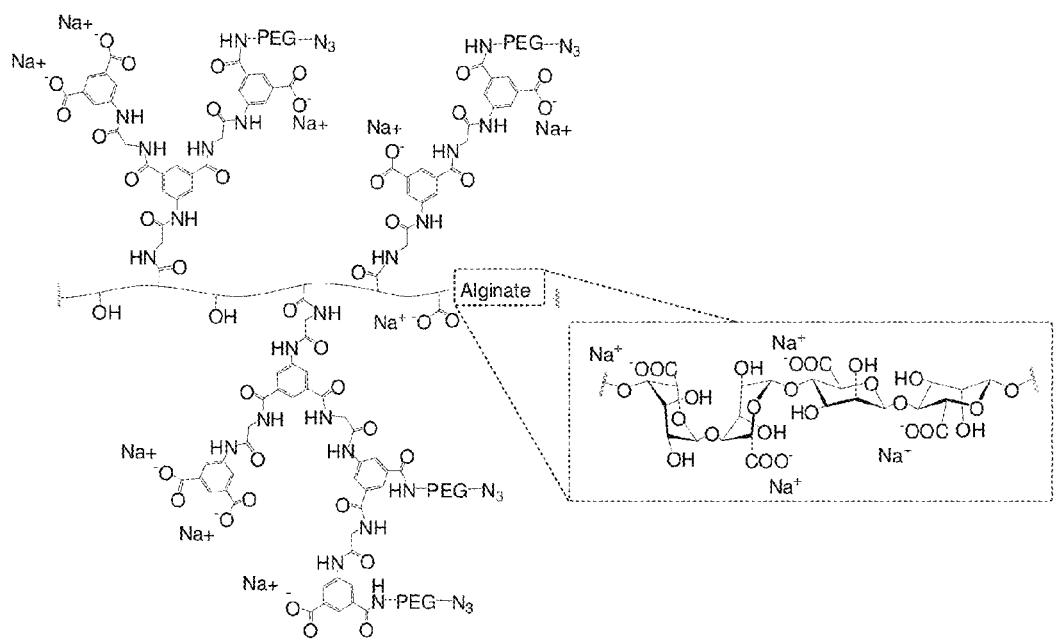
FIG. 14B is a diagram of an azido-functionalized hyperbranched alginate.

Graphical illustrations of these two highly branched and functional polymers are shown in FIGS. 14A and 14B. More specifically, FIG. 14A shows a functionalized PAMAM dendrimer, where generation 2 is shown for simplicity. FIG. 14B shows an azido-functionalized hyperbranched alginate.

Figure 15:
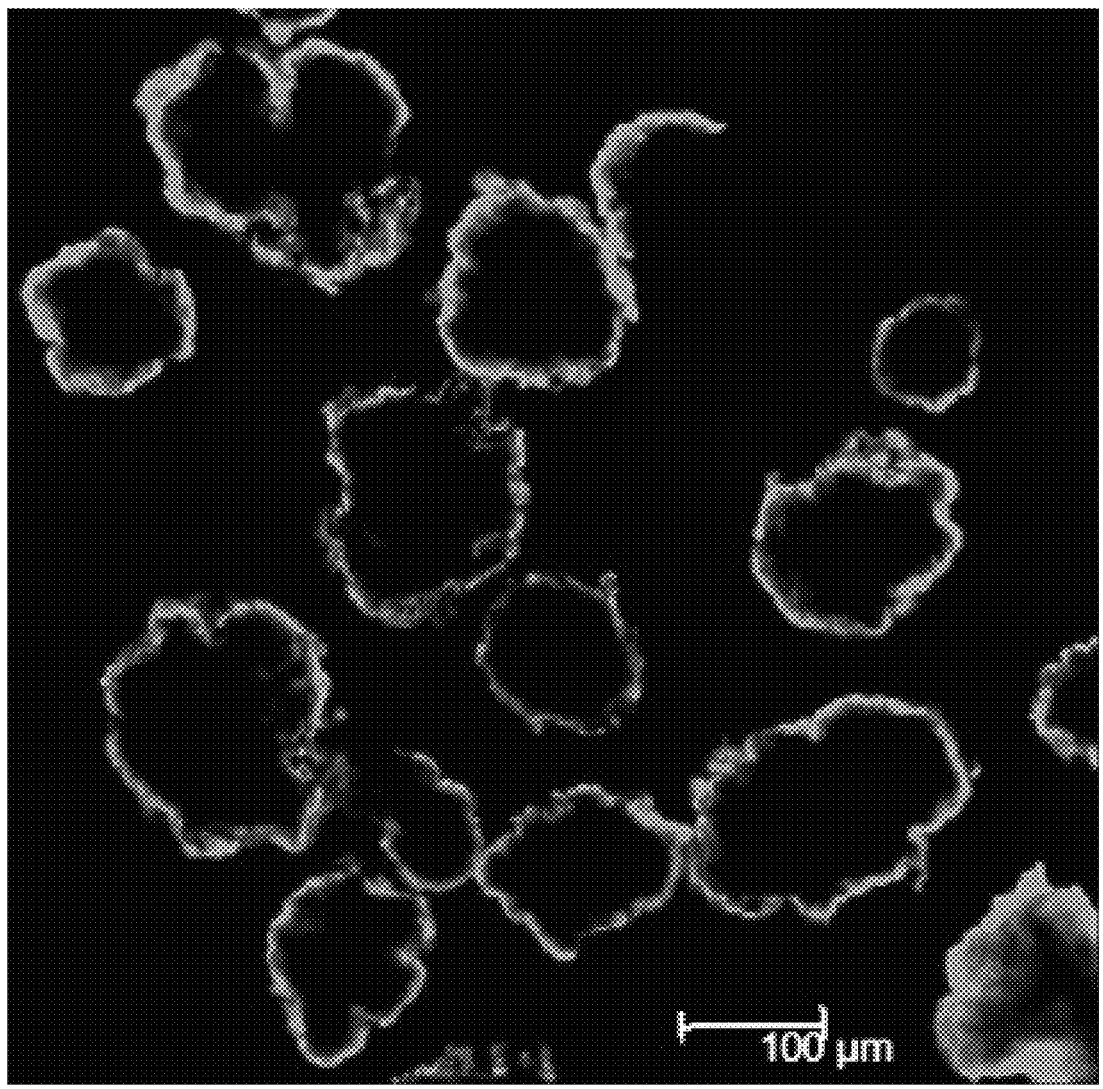
FIG. 15 is a confocal cross-section image revealing the fluorescent capsule of 6 layers deposited around on rat pancreatic islets.

Alternate deposition of these two polymeric materials (2 mg/mL, various aqueous buffers) resulted in the successful encapsulation of rat pancreatic islets as shown in the fluorescence image on FIG. 15. More specifically, FIG. 15 shows a confocal cross-section image revealing the fluorescent capsule of 6 layers deposited around on rat pancreatic islets. These capsules can serve as semipermeable protective barriers aiming to aid immunoisolation of cells during islet transplantation procedures without imposing significant thicknesses to impede nutrient diffusion. Fluorescent labeling of the polymers permit evaluation of the capacity of these polymers for variety of chemical functionality in one system arising from large number of available functional groups on the branched materials. Either covalent of a combination of covalent and electrostatic interactions were utilized to assemble the coatings. Multilayer coatings were stable over time. Minor cytotoxicity was observed when using the positively charged polymers, which is common for polycations; however, cell viability was improved by decreasing polymer concentration, net positive charge, and incubation time.

Coated islets remained functional, as they released insulin in response to glucose (FIG. 15) and were functionally comparable to naked islets even after 4 h of stimulated insulin release.

Figure 16:
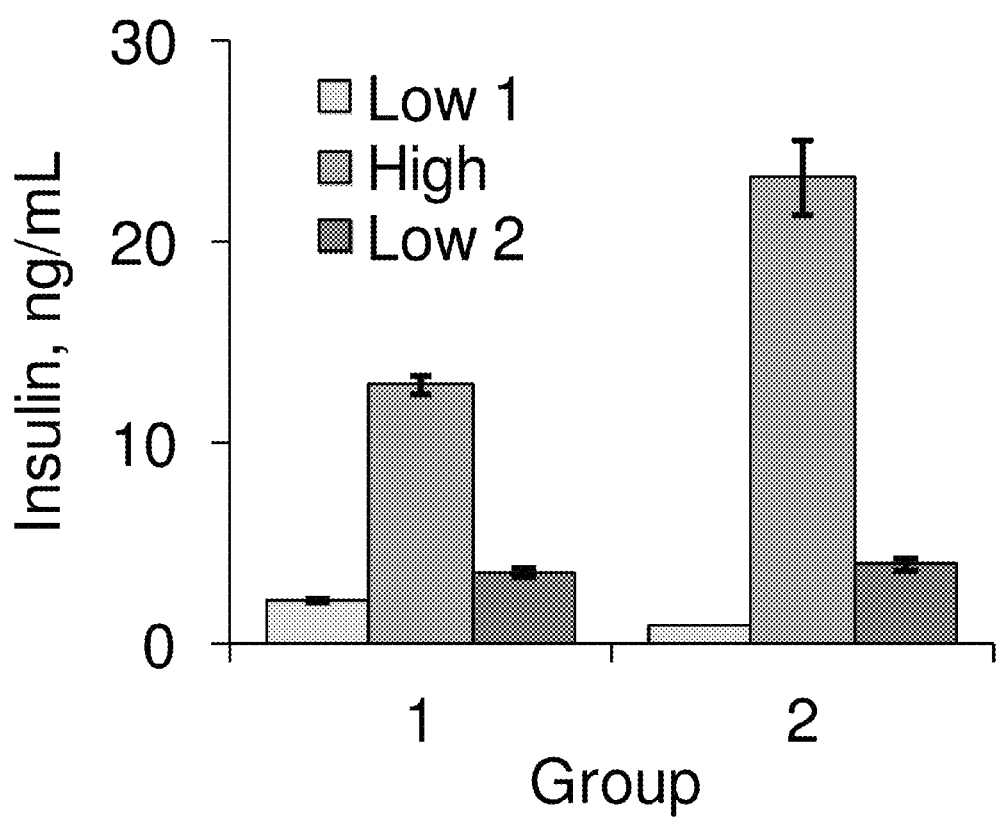
FIG. 16 is a chart showing an amount of insulin released by islets upon incubation in low (60 mg/dL), high (300 mg/dL), and low glucose containing buffer for 1 h each. Group 1 are the control islets (no coating), while group 2 is the nano-scale encapsulated islets.

FIG. 16 shows a amount of insulin released by islets upon incubation in low (60 mg/dL), high (300 mg/dL), and low glucose containing buffer for 1 h each. Uncoated islets (group 1) and islets coated with 6 layers (group 2) are shown.

Figure 17:
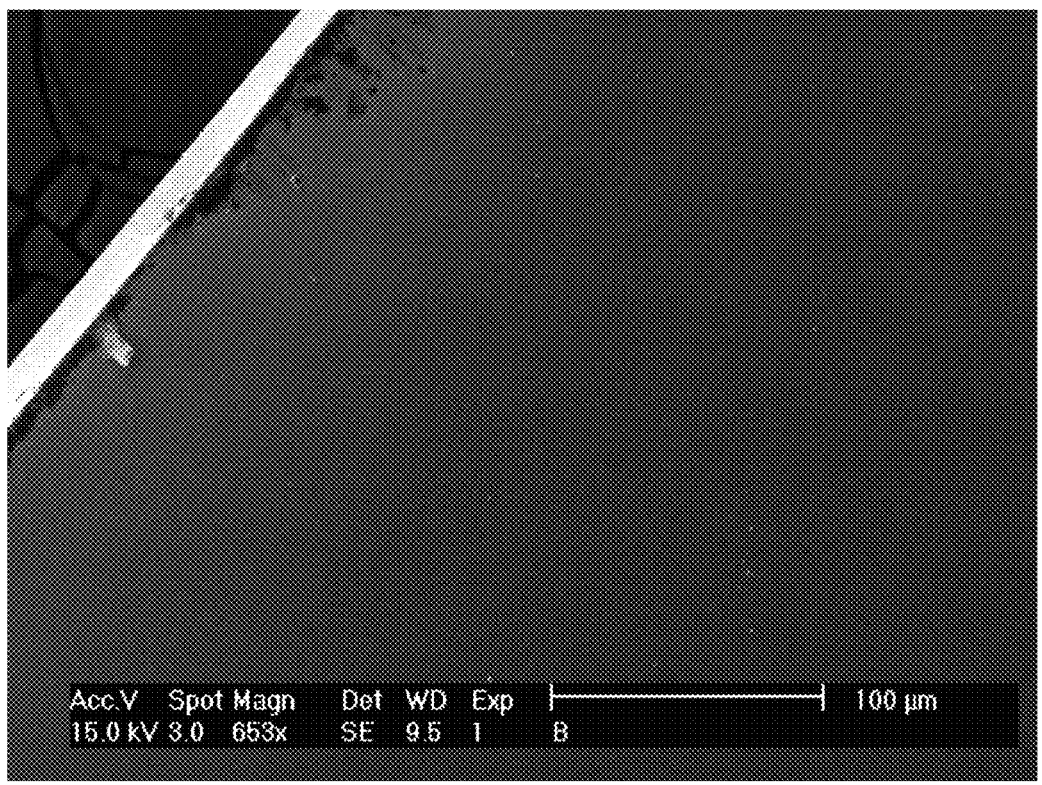
FIG. 17 is an electron microscopic image of a 12 layer film deposited on Si wafer.

FIG. 17 shows an electron microscopic image of a 12 layer film deposited on Si wafer.

To further evaluate such coating films, multiple layers were deposited on Si wafer resulting in highly homogeneous film topographies (FIG. 16) and linear (R2 0.99) increase on film thickness with each deposited layer (FIG. 17). Si wafers were azido functionalized via silanization with 11-bromoundecyl-trichlorosilane followed by sodium azide treatment. Washing of wafers with highly ionic solutions did not affect the polymer thickness, illustrating the superior stability of these convalently linked layers.

Figure 18:
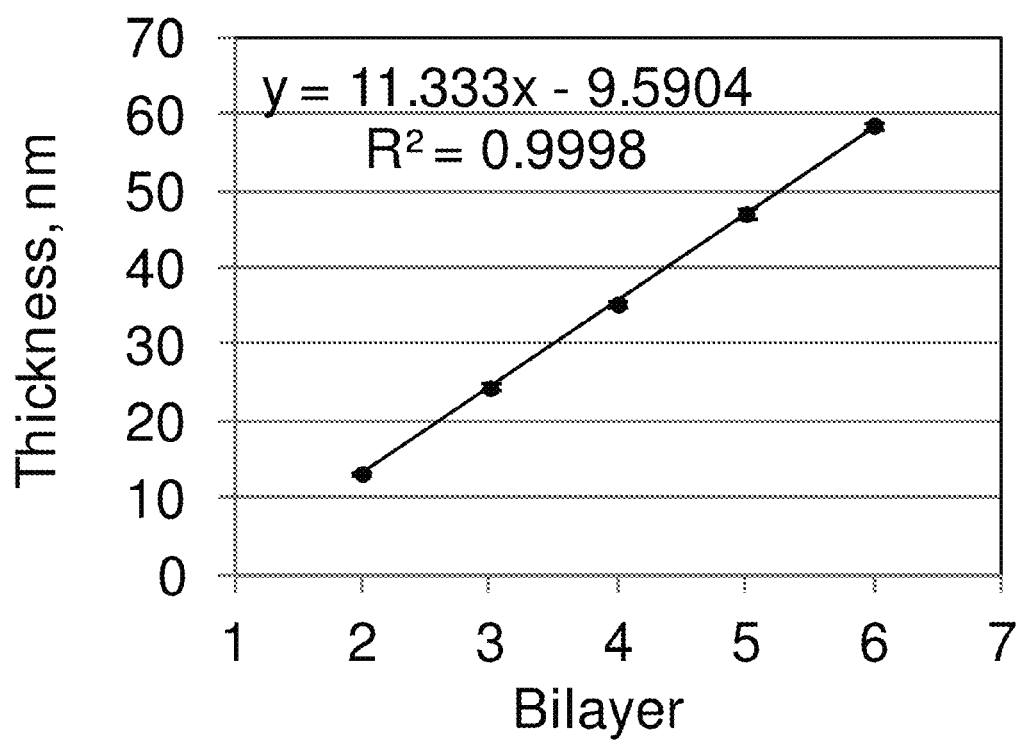
FIG. 18 is a chart showing the film thickness increase upon deposition of a bilayer on the azido-functionalized Si wafer.

FIG. 18 shows the film thickness increase upon deposition of a bilayer on the azido-functionalized Si wafer. A bilayer consisted of one layer of the functionalized PAMAM dendrimer and one layer of the functionalized hyperbranched alginate.

It is to be understood that while the invention in has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

We claim:

1. A protective coating for covering a biological material, the protective coating comprising a plurality of interconnected layers covalently bonded to each other, wherein the plurality of interconnected layers comprise:
   at least one hyperbranched alginate, and
   at least one dendrimer.

2. The protective coating of claim 1, further comprising at least one biologically-active agent chemoselectively presented on a surface of the coating.

3. The protective coating of claim 2, wherein the biologically-active agent is one selected from a targeting agent, a labeling agent, a bioactive interface, and combinations thereof.

4. The protective coating of claim 1, wherein the biological material is one selected from the group consisting of a plurality of cells, a plurality of cell clusters, a plurality of bioactive agents, and combinations thereof.

5. The protective coating of claim 1, wherein the at least one hyperbranched alginate comprises an azido-functionalized hyperbranched alginate.

6. The protective coating of claim 1, wherein the at least one dendrimer comprises a poly(amido)amine dendrimer.

7. The protective coating of claim 5, wherein the at least one dendrimer comprises a poly(amido)amine dendrimer.

* * * * *